United States Patent
St. Louis et al.

(10) Patent No.: US 10,881,490 B2
(45) Date of Patent: Jan. 5, 2021

(54) HANDPIECE MAINTENANCE SYSTEM AND DENTAL INSTRUMENTS FOR PREDICTIVE MAINTENANCE

(71) Applicant: KAVO DENTAL TECHNOLOGIES, LLC, Charlotte, NC (US)

(72) Inventors: Robert Thomas St. Louis, Charlotte, NC (US); Michael Carl Dunaway, Charlotte, NC (US); Steven Bohon, Charlotte, NC (US); Mitchell James Rutledge, Mount Holly, NC (US)

(73) Assignee: KAVO DENTAL TECHNOLOGIES, LLC, Charlotte, NC (US)

( * ) Notice: Subject to any disclaimer, the term of this patent is extended or adjusted under 35 U.S.C. 154(b) by 636 days.

(21) Appl. No.: 15/618,037

(22) Filed: Jun. 8, 2017

(65) Prior Publication Data
US 2018/0353275 A1 Dec. 13, 2018

(51) Int. Cl.
*A61C 19/00* (2006.01)
*A61C 1/00* (2006.01)
(Continued)

(52) U.S. Cl.
CPC .......... *A61C 19/002* (2013.01); *A61C 1/0007* (2013.01); *A61C 1/0015* (2013.01);
(Continued)

(58) Field of Classification Search
CPC ..... A61C 19/02; A61C 19/002; A61C 1/0061; A61C 1/06
See application file for complete search history.

(56) References Cited

U.S. PATENT DOCUMENTS

| 4,990,087 A * | 2/1991 | De Rocchis | ........ | A61C 19/002 433/104 |
| 7,258,546 B2 | 8/2007 | Beier et al. | | |

(Continued)

FOREIGN PATENT DOCUMENTS

| DE | 10225232 A1 | 12/2002 |
| EP | 2327370 A2 | 6/2011 |

(Continued)

OTHER PUBLICATIONS

KaVo Dental GmbH "KaVo Estetica E70/E80 Vision: Get in touch with your vision." Product Brochure, 13 pages (Mar. 2015).

(Continued)

*Primary Examiner* — Kevin Joyner
(74) *Attorney, Agent, or Firm* — Michael Best & Friedrich LLP

(57) ABSTRACT

A handpiece maintenance system and method identifies a dental handpiece and operates in a diagnostic cycle to power the handpiece and determine predictive maintenance condition thereof. The handpiece maintenance system includes a temperature sensor and/or an acceleration sensor to measure the conditions of the handpiece during the diagnostic cycle. The predictive maintenance condition of the handpiece is based on data from the diagnostic cycle and other stored data for the identified handpiece. A system is also configured to determine a predictive maintenance condition of the handpiece based on sensor data read from a handpiece and historical usage data thereof.

6 Claims, 21 Drawing Sheets

(51) Int. Cl.
*A61C 1/06* (2006.01)
*A61C 1/18* (2006.01)
*G16H 40/63* (2018.01)

(52) U.S. Cl.
CPC .............. *A61C 1/0061* (2013.01); *A61C 1/06* (2013.01); *A61C 1/181* (2013.01); *G16H 40/63* (2018.01); *A61C 2204/005* (2013.01)

(56) References Cited

U.S. PATENT DOCUMENTS

| | | |
|---|---|---|
| 7,435,398 B2 | 10/2008 | Lund-Jensen et al. |
| 2004/0209223 A1 | 10/2004 | Beier et al. |
| 2006/0196728 A1 | 9/2006 | Numakawa et al. |
| 2007/0038206 A1 | 2/2007 | Altshuler et al. |
| 2009/0322541 A1 | 12/2009 | Jones et al. |
| 2014/0184397 A1 | 7/2014 | Volpert |
| 2015/0125809 A1 | 5/2015 | Pruckner et al. |
| 2015/0147718 A1* | 5/2015 | Khakpour .............. A61C 17/20 433/81 |
| 2015/0254550 A1* | 9/2015 | Voillat ................. A61C 19/002 377/15 |
| 2015/0377969 A1 | 12/2015 | Muto et al. |

FOREIGN PATENT DOCUMENTS

| | | |
|---|---|---|
| EP | 2965709 A1 | 1/2016 |
| EP | 2514386 B1 | 3/2016 |
| EP | 2745803 B1 | 4/2016 |
| EP | 2536442 B1 | 7/2016 |
| WO | 2012032190 A1 | 3/2012 |
| WO | 2016/005416 A1 | 1/2016 |

OTHER PUBLICATIONS

International Search Report and Written Opinion for Application No. PCT/US2018/036098 dated Sep. 20, 2018 (14 pages).

* cited by examiner

HANDPIECE MAINTENANCE SYSTEM AND DENTAL INSTRUMENTS FOR PREDICTIVE MAINTENANCE

BACKGROUND

Embodiments relate to a handpiece maintenance system having a diagnostic cycle to determine a predictive maintenance condition of handpieces and to monitoring the performance of handpieces by sensing and storing data thereon.

SUMMARY

One embodiment provides a dental handpiece maintenance system for maintaining a handpiece that includes a housing, an entrance for providing access to a chamber in the housing, at least one maintenance coupling disposed in the chamber that is sized to receive a handpiece. The dental handpiece maintenance system further includes an electronic processor that is configured to: receive inputs from a user interface, operate a maintenance cycle for the handpiece disposed within the dental handpiece maintenance system, operate the handpiece in a diagnostic cycle while receiving one or more conditions of the handpiece, and determine a predictive maintenance condition for the handpiece from the sensed conditions during the diagnostic cycle.

Another embodiment provides a method of operating a dental handpiece maintenance system having a housing and at least one maintenance coupling for receiving a dental handpiece comprising providing a handpiece secured on the maintenance coupling disposed in a chamber of the dental handpiece maintenance system. The method further includes operating the dental handpiece maintenance system in a maintenance cycle, operating the handpiece in a diagnostic cycle while sensing one or more conditions of the handpiece, and determining a predictive maintenance condition for the handpiece from the one or more conditions sensed during the diagnostic cycle.

Another embodiment provides a dental handpiece maintenance arrangement for maintaining a handpiece comprising: a dental handpiece maintenance system including a housing, an entrance for providing access to a chamber in the housing, at least one maintenance coupling disposed in the chamber, the maintenance coupling sized to receive a handpiece, and an electronic processor. The electronic processor is configured to: receive inputs from a user interface, operate a maintenance cycle for the handpiece disposed within the dental handpiece maintenance system, and operate the handpiece in a diagnostic cycle while receiving one or more conditions of the handpiece. The arrangement includes a predictive maintenance determining device for determining a predictive maintenance condition for the handpiece from the one or more conditions received during the diagnostic cycle.

Other aspects will become apparent by consideration of the detailed description and accompanying drawings.

DETAILED DESCRIPTION

Before any embodiments are explained in detail, it is to be understood that they are not limited in their application to the details of construction and the arrangement of components set forth in the following description or illustrated in the following drawings. Other embodiments are possible and embodiments explained are capable of being practiced or of being carried out in various ways.

Figure 1:
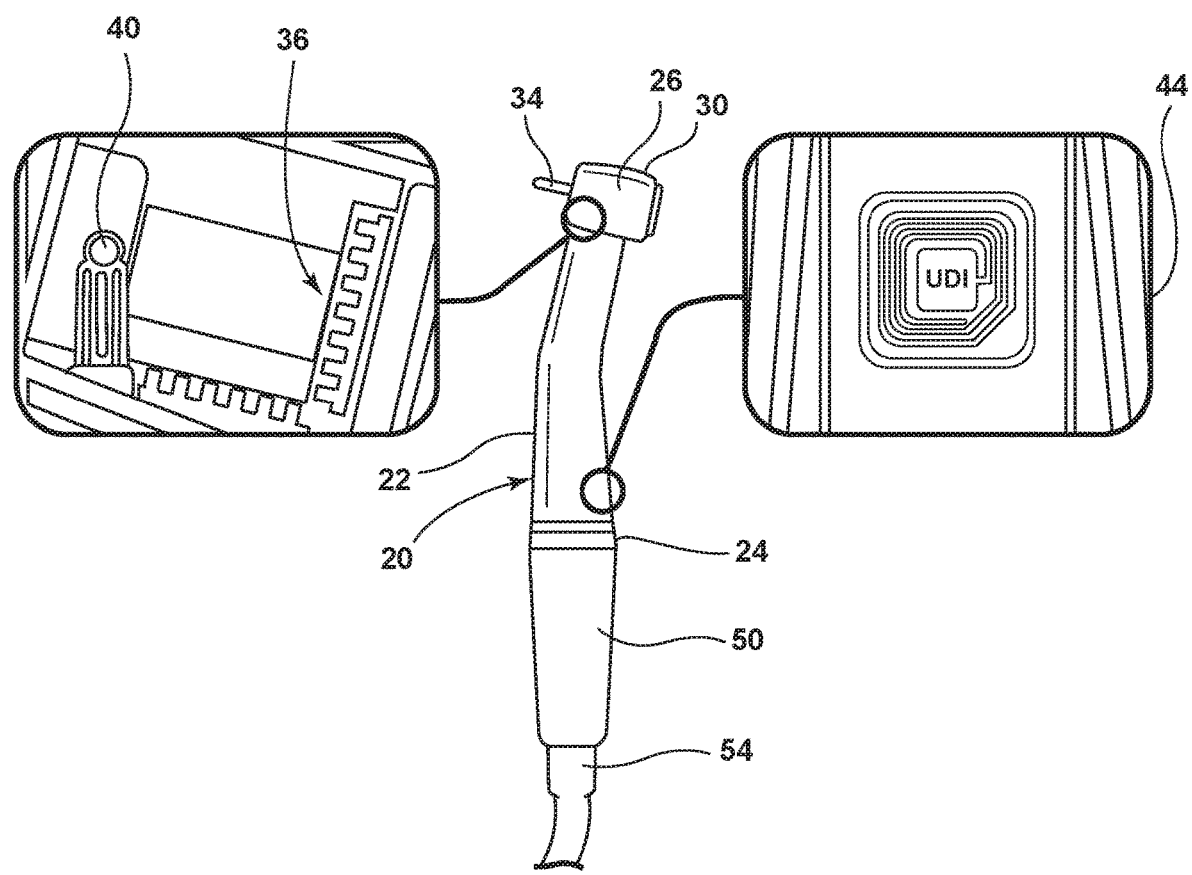
FIG. 1 illustrates a front view of a handpiece.

FIG. 1 illustrates a handpiece 20 including a housing 22 having a first end 24 and a second end 26 with an end cap 30. The end cap 30 has a tool 34, such as a burr, attached thereto. The expanded view at the second end 26 of the handpiece 20 shows gearing 36 and a temperature sensor 40, such as a thermal sensor, that are disposed within the handpiece. The gearing 36 drives the tool 34. A unique device identifier (UDI) 44 is shown in the expanded view at the first end 24 of the handpiece 20. A coupler 50 is secured to the first end 24 of the handpiece 20. The coupler 50 includes a power cord 54 for providing electrical or pneumatic power to the handpiece 20. In other embodiments, the power cord 54 provides light and/or irrigation fluid to the handpiece 20.

Figure 2:
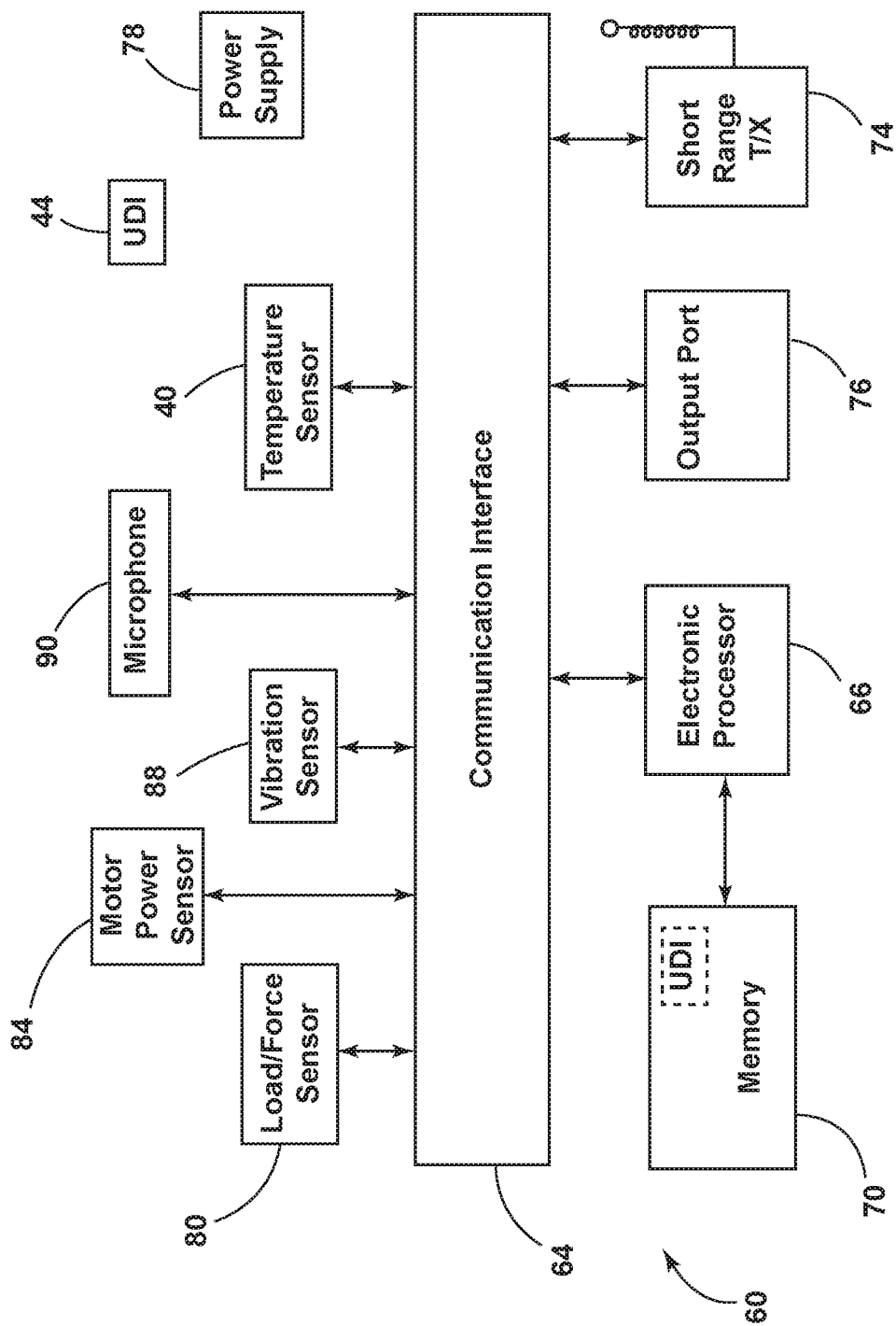
FIG. 2 illustrates a block diagram of one embodiment of the handpiece.

FIG. 2 illustrates a control system 60 of one embodiment of the handpiece 20. In the example shown, the control system 60 includes a communication interface 64, such as a communication bus, for providing communication between an electronic processor 66 and various components. In one embodiment, a handpiece memory 70 is electrically connected to the electronic processor 66. Software stored in the handpiece memory 70 may include instructions stored on a non-transitory computer-readable medium, that when executed, cause the electronic processor 66 to perform some or all of the methods described herein. In some embodiments, the electronic processor 66 is one of a microcontroller, a microprocessor, an application-specific integrated circuit ("ASIC"), or other suitable processing device. In some embodiments, the handpiece memory 70 is a non-transitory computer-readable medium including random access memory ("RAM"), read-only memory ("ROM"), or other suitable non-transitory computer-readable medium.

In the FIG. 2 embodiment, the UDI 44 is separate from the handpiece memory 70. In one embodiment, the UDI 44 is a passive radio frequency identification (RFID) chip. In other embodiments, the UDI 44 is an active RFID chip. In the embodiment illustrated in FIG. 2, the unique device identifier 44 includes identification data intended to be permanently stored in the handpiece memory 70. The data in the handpiece memory 70 is read, along with sensor data, by another device. In one embodiment, the software stored in the memory 70 is executed by the electronic processor 66.

The handpiece 20 includes a short range transceiver 74 for communication with external devices. The short range transceiver 74 may include a one or more of a BLUETOOTH transceiver, a near-field communications (NFC) transceiver, a radio frequency (RF) transceiver, a Wi-Fi 802.11 transceiver, or other suitable wireless transceiver. In one embodiment, the handpiece memory 70, the electronic processor 66, the short range transceiver 74 and the communication interface 64 are components of an active or passive RFID chip embodiment. One or more sensors are connected thereto or integrated into the RFID chip. Further, in one embodiment the handpiece 20 includes an output port 76 for an electrical communication connection.

FIG. 2 illustrates a load/force sensor 80 disposed in the handpiece 20 that detects force applied to the tool 34. In one embodiment, the force is an axial force applied to the tool 34. FIG. 2 illustrates an electric motor power sensor 84 that senses current and/or voltage for an electric motor that in one embodiment is disposed in the handpiece 20 to drive the gearing 36, and thus the tool 34. An example of an electric motor disposed in a handpiece is set forth in U.S. Pat. No. 8,487,488, the disclosure of which is hereby incorporated by reference.

FIG. 2 illustrates an embodiment including a vibration sensor 88, such as an accelerometer, that senses vibration of the handpiece 20. In FIG. 2, a microphone 90 senses audible vibrations of the handpiece 20. The temperature sensor 40 senses temperature at the second end of the handpiece 20. Additional or different temperature sensors for sensing the temperature of other components, such as the head, the chuck, the bearings, and the drive shafts of the handpiece 20 are provided in other embodiments. In one embodiment, the electronic processor 66 logs and stores with a time stamp the vibration and/or temperature data as usage data in the memory 70 of the handpiece 20 during operation of the handpiece 20.

While the above sensors are illustrated as secured to the handpiece 20, other arrangements are contemplated. For instance, in one embodiment the motor power sensor 84 is located at a location where power is provided to the power cord 54 to measure voltage and/or current provided thereto. For instance, in one embodiment the coupler 50 includes an electric motor that drives the handpiece 20. Voltage and current for a three-phase motor (for example, U, V, and W phases) is determined and stored. Rotation of a magnet mounted on a drive shaft is sensed by Hall effect sensors to determine a rotation speed and a position of the electric motor and the handpiece 20. In another embodiment, a pneumatic powered motor is disposed in the coupler 50 and pneumatically drives a drive shaft of the handpiece 20. In some embodiments, the temperature sensor 40 is a thermocoupler mounted externally or internally to the handpiece 20.

A power supply 78 is provided within the handpiece 20 to power an electrical circuit including the individual components as shown in FIG. 2. The power supply 78 provides voltage to the individual components that require power. The power supply 78 is one or more of a battery, a rechargeable battery, and a power receiver that receives electrical power from the power cord 54.

Figure 3:
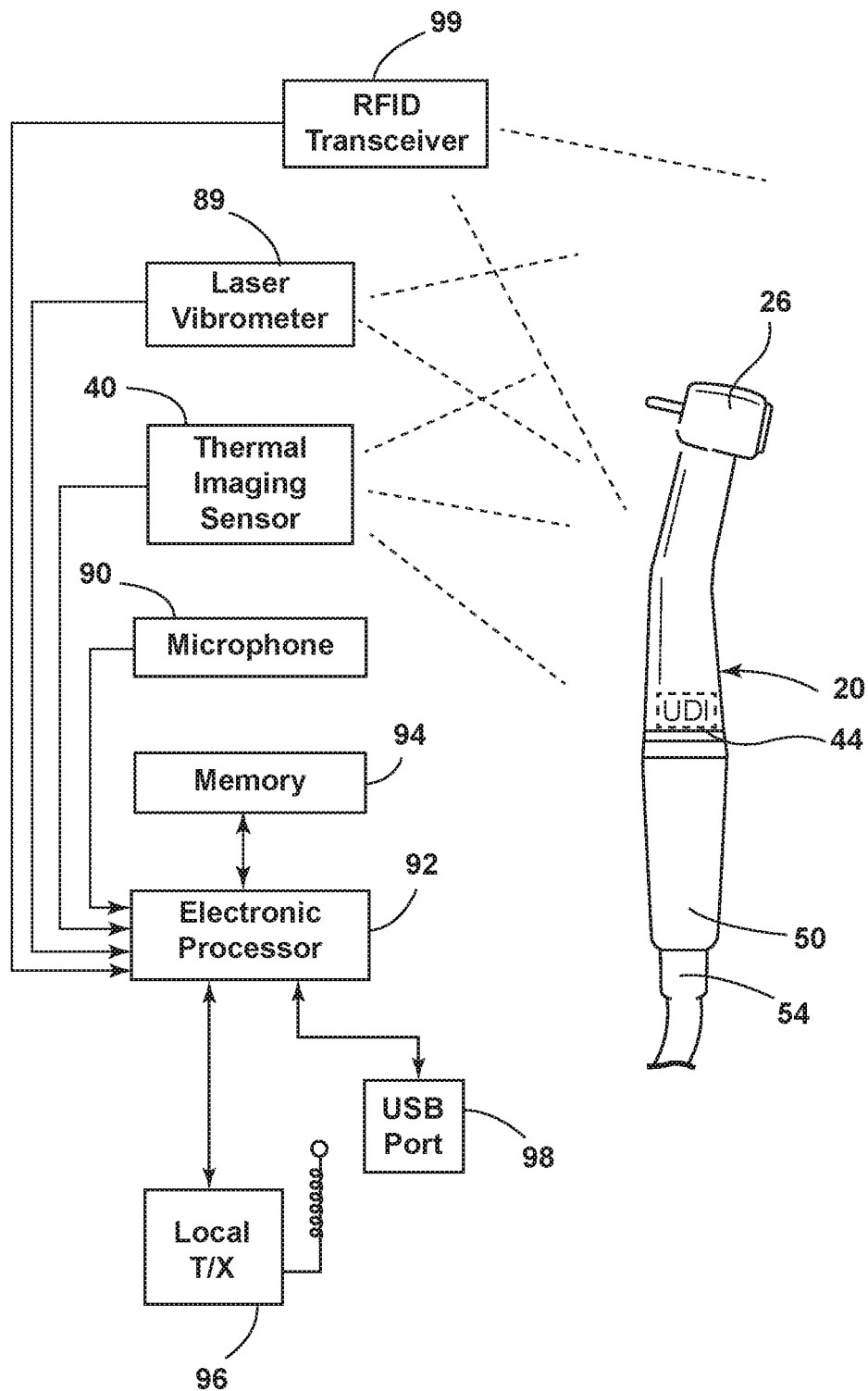
FIG. 3 illustrates a block diagram of sensors mounted near a handpiece.

In the embodiment shown in FIG. 3, the vibration sensor is a laser vibrometer 89 that is mounted onto a treatment unit near a location where the handpiece 20 is used during a procedure to measure vibration of the handpiece 20 from a distance. In FIG. 3, the microphone 90 is mounted onto a treatment unit near a location where the handpiece 20 is used during a procedure. Finally, the temperature sensor 40 shown in FIG. 3 is a thermal imaging sensor secured to the treatment unit near the handpiece 20 for optically measuring temperature of the handpiece by thermal imaging and/or infrared detection. In one embodiment, the laser vibrometer 89, the microphone 90, and the thermal imaging sensor 40 are provided on an external attachment of the treatment unit to be positioned near an area of use for the handpiece 20.

FIG. 3 illustrates an embodiment with the laser vibrometer 89, the thermal imaging sensor 40 and the microphone 90 providing sensed data to an electronic processor 92. In one embodiment, the data is stored in a memory 94 repeatedly with a time stamp to obtain a log or historical record for the usage data of the properties measured for later use. In other embodiments, the historical usage data is output essentially in real time via a local wireless transceiver 96 or stored for later output via a wired connection to an external port 98. In another embodiment, the sensors 40, 88, 90 are individually provided with hard wired communication to a remote electronic controller to provide sensor data for processing, and thus the electronic processor 92 and the memory 94 are not necessary.

In one embodiment, the group of sensors includes a short range RFID transceiver 99 that detects and reads the identity data for the specific handpiece 20. Thus, the data sensed by the laser vibrometer 89, thermal imaging sensor 40, and microphone 90 is matched to the identified handpiece 20 for immediate or later processing.

While both of FIGS. 2 and 3 show each of the sensors arranged to store usage data with a time stamp in memory 70, 94, in other embodiments, the individual sensors 40, 80, 88, 90 each have their own non-transitory memory that is readable and erasable by a read/write device. Further, the sensors and other elements of FIG. 3 are connected by a communication interface, such as a communication bus, in one embodiment.

In another embodiment, the electric motor is disposed in the coupler 50 and detachable from the handpiece 20. The motor power sensor 84 is also disposed in the coupler 50 and provides voltage and/or current data to one of its own memory, the memory of the handpiece 20, or directly to a remote electronic controller via a hard wired or a wireless communication.

Figure 4:
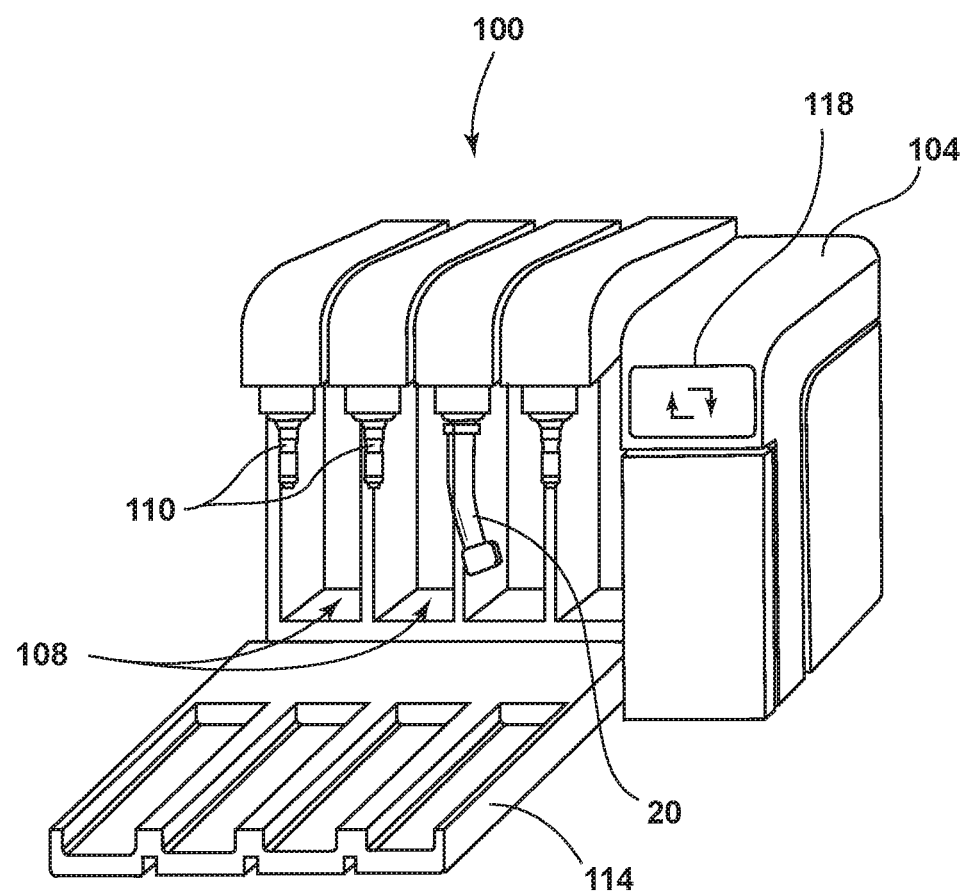
FIG. 4 illustrates a perspective view of a dental handpiece maintenance system.

FIG. 4 illustrates an exemplary dental handpiece maintenance system 100 that includes a housing 104 and a plurality of chambers 108 having maintenance couplings 110 for receiving a handpiece 20. A handpiece 20 shown in FIG. 4 is secured to a maintenance coupling 110. An entrance 114, for example a door in one embodiment, provides access to the chambers 108 to enable maintenance of the handpieces 20. A display 118 displays the status of the dental handpiece maintenance system 100 and additional information. The dental handpiece maintenance system 100 includes other components for applying cleaning agents to the handpieces 20, and otherwise treating the handpieces that are not related to predictive maintenance, and thus not further described herein.

Figure 5:
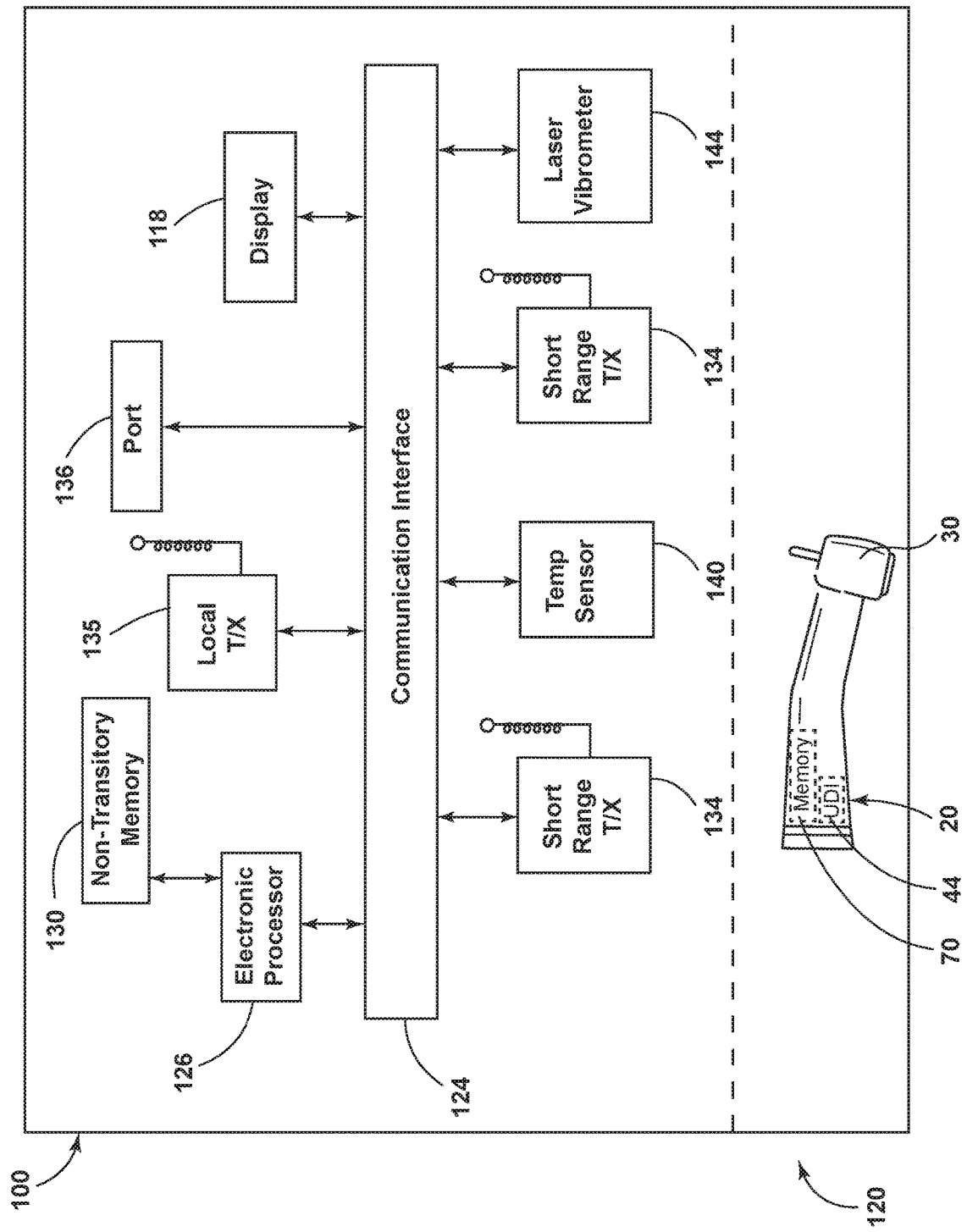
FIG. 5 illustrates a block diagram of the dental handpiece maintenance system.

FIG. 5 is a block diagram 120 of an embodiment of the dental handpiece maintenance system 100 for maintaining a handpiece 20 disposed therein. The block diagram 120 shows a communication interface 124, such as a communication bus, for providing communication between an electronic processor 126 and various components as shown in FIG. 5. A non-transitory memory 130 that stores programs for execution by the electronic processor 126 is in communication therewith. In the FIG. 5 embodiment, the dental handpiece maintenance system 100 includes a short range transceiver 134 for communication with the UDI 44 and the short range transceiver 74 of the handpiece 20. Data read from the handpiece 20 is stored in memory 130 by the electronic processor 126 of the dental handpiece maintenance system 100. Further, the data is transmitted to an electronic controller via a local transceiver 135 or is capable of transmission via an output port 136 for an electrical communication connection in one embodiment. The local transceiver 135 communicates over a WI-FI or another communication network providing similar results. In one embodiment, the dental handpiece maintenance system 100 includes one or more of a temperature sensor 140 and a laser vibrometer 144 in the chambers 108 for determining properties of the handpiece 20 during maintenance cycles. In one embodiment, the temperature sensor 140 is a thermal imaging sensor.

Figure 6:
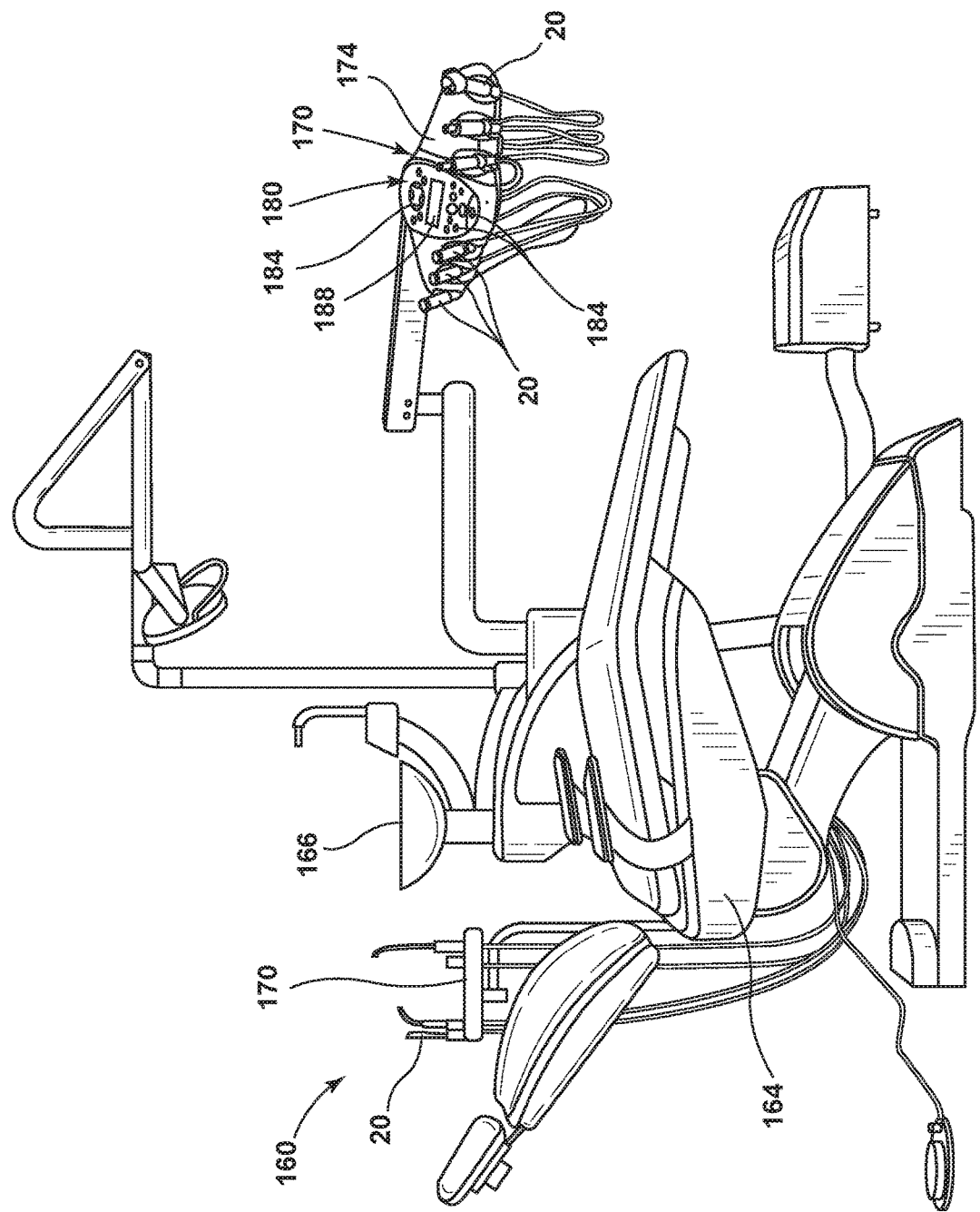
FIG. 6 illustrates a perspective view of a treatment unit.

FIG. 6 illustrates one embodiment of a treatment unit 160 that utilizes the handpiece 20. The treatment unit 160 includes a powered chair 164. A sink 166 is separately disposed in a room containing the treatment unit 160. The treatment unit 160 shown in FIG. 6 includes two delivery units 170 that support multiple handpieces 20. One delivery unit 170 includes a tray 174 with holders formed therein for receiving and storing the handpieces 20 when not in use. The delivery unit 170 includes an electronic controller 180 having input controls 184 and a display 188.

Figure 7:
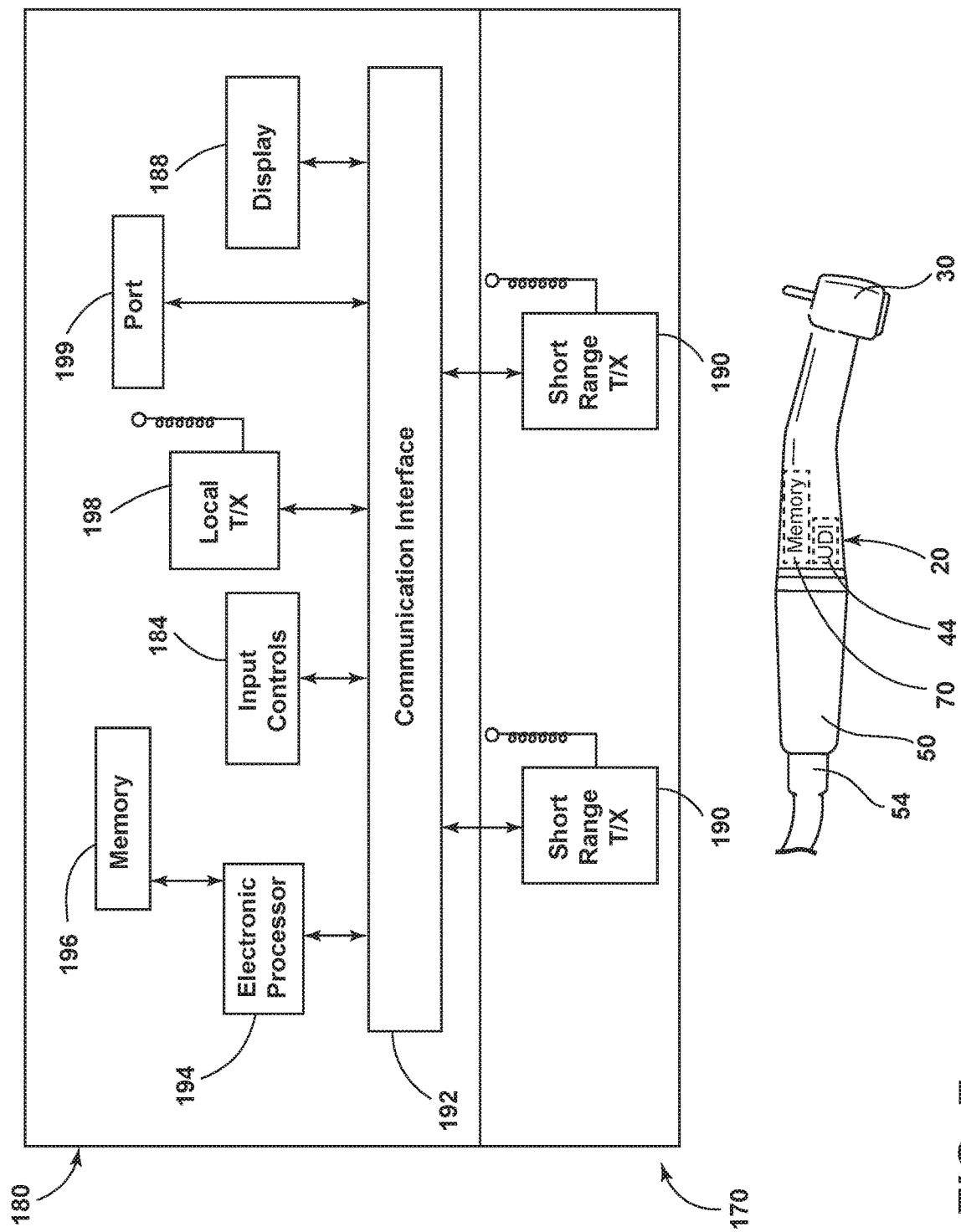
FIG. 7 illustrates a block diagram of a delivery unit.

FIG. 7 is a block diagram of the delivery unit 170, including the electronic controller 180. Local or short range transceivers 190 disposed on or within the tray 174 read/write to the handpiece memory 70 and UDI 44 of a handpiece 20. The short range transceivers 190 communicate via a communication interface 192, such as a communication bus, with an electronic processor 194. The communication interface 192 shown in FIG. 7 provides for communication between the electronic processor 194 and various components including a non-transitory memory 196. As shown in FIG. 7, the electronic controller 180 includes a local transceiver 198 for communication with external devices. The local transceiver 198 communicates over a WI-FI or another communication network providing similar results. Likewise, the electronic controller 180 includes an input/output port 199 for an electrical communication connection in one embodiment. Besides the electronic controller 180 operating to control the handpieces 20 connected to the delivery unit 170, the electronic controller reads data from the handpiece memory 70 and processes and/or transmits the data via the local transceiver 198 or an input/output port 199 in a similar manner as the dental handpiece maintenance system 100 discussed above.

Figure 8:
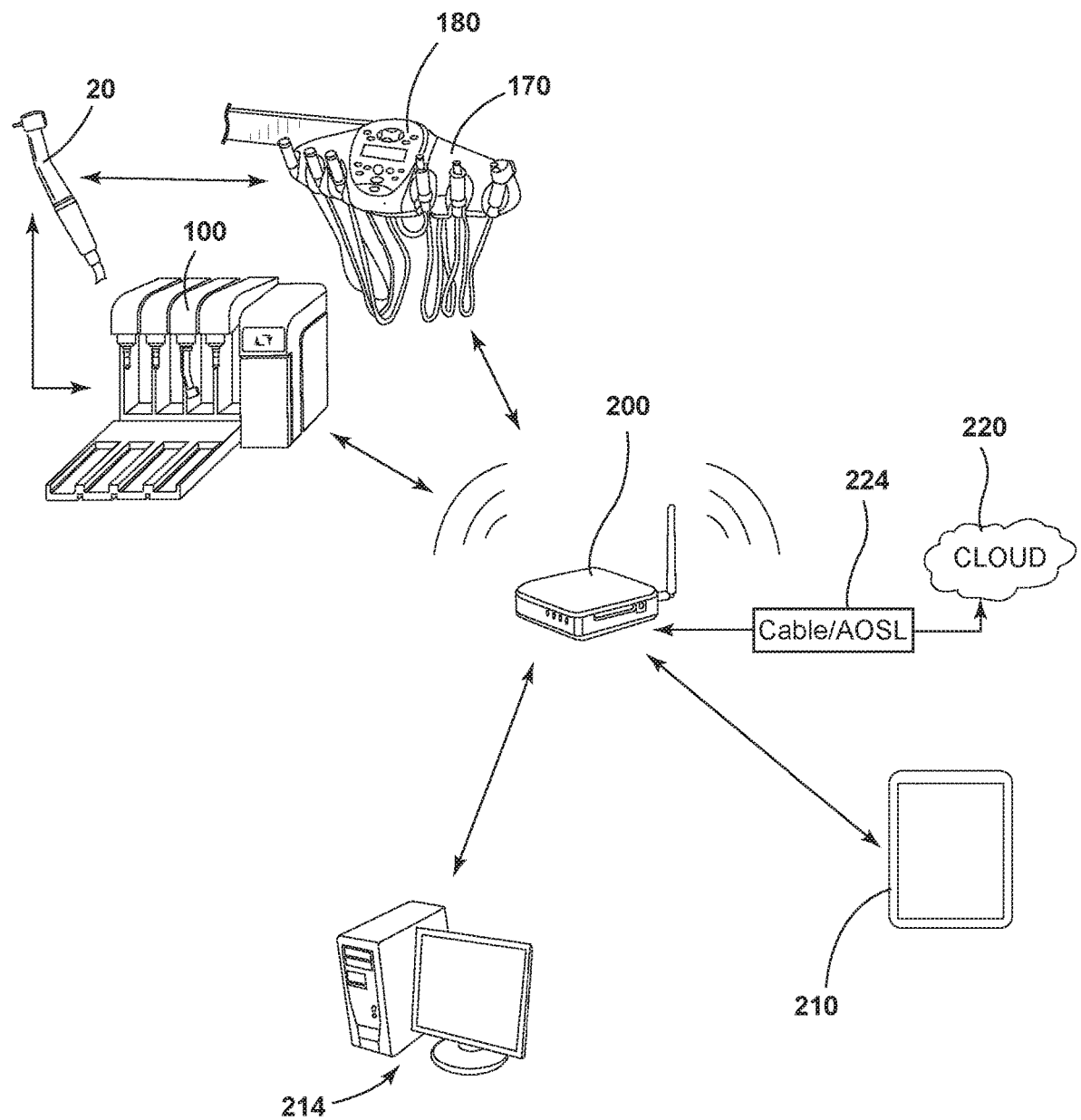
FIG. 8 illustrates a communication diagram for components including a dental handpiece maintenance system, a portable universal controller, a desk top computer, and a cloud computer.

FIG. 8 illustrates a communication diagram for a handpiece 20 with one of a dental handpiece maintenance system 100 or an electronic controller 180 of a delivery unit 170 and additional communication via a network access point 200 with one or more of a portable universal controller 210, a computer work station 214, and a cloud computer 220 via a cable 224 or other connection, such as an internet connection. The dental handpiece maintenance system 100 is configured for reading of sensor data from the handpiece memory 70 and the UDI 44 of the handpiece 20 with the short range transceiver 134 as shown in FIG. 4 via Bluetooth or a different short range interconnection. Likewise, the delivery unit 170 with the short range transceivers 190 using Bluetooth, as shown in FIG. 7, is capable of reading the sensor data from the handpiece memory 70 and reading the UDI 44 of the handpiece 20 via the short range transceiver 74 of the handpiece 20.

Accordingly, FIG. 8 illustrates one embodiment for providing communication between components of a treatment unit 160, such an electronic controller 180 of a delivery unit 170 or a dental handpiece maintenance system 100, with a portable universal controller 210, a computer work station 214, and/or a cloud computer 220 via a network access point 200. Other embodiments include direct wired connections, various mid and long range wireless connections and various computer networks.

Handpiece Operation

Figure 9:
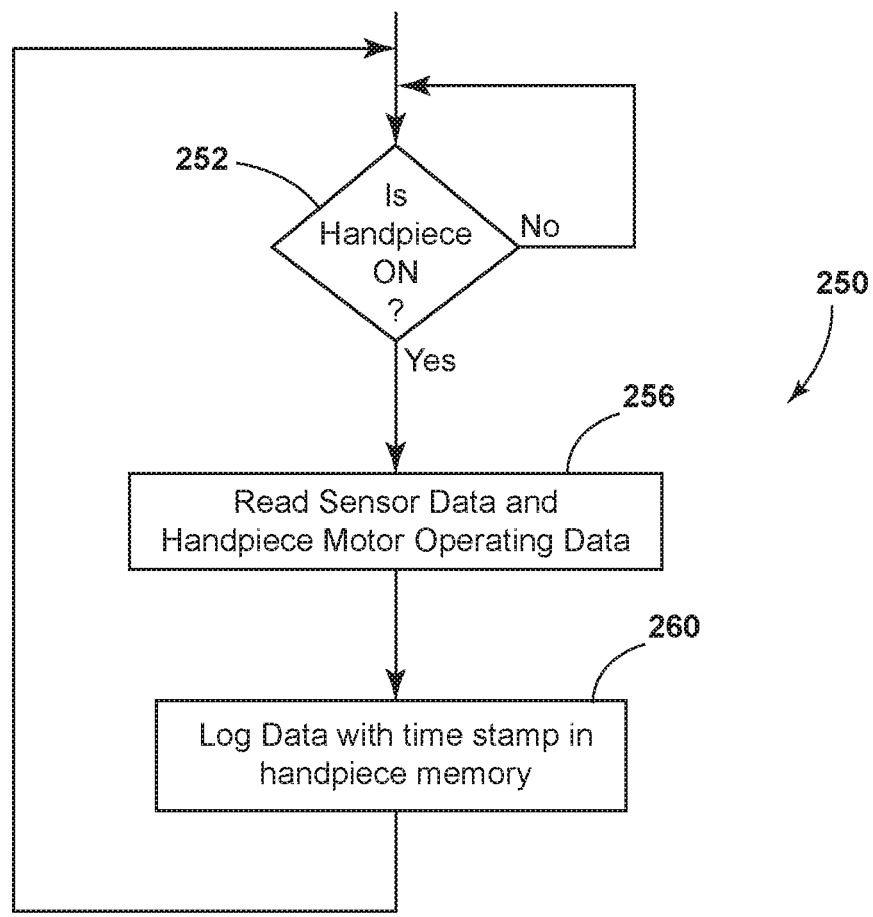
FIG. 9 illustrates a flow chart for sensors operating with the handpiece of FIGS. 1 and 2.

In one embodiment, operation of the handpiece 20 is monitored as shown in the method set forth in flow chart 250 of FIG. 9. The electronic processor 66 of the handpiece 20 executes a program or is otherwise configured to determine whether the handpiece is powered for usage (step 252). If no electricity or pneumatic power is being received, even in an idle state, the electronic processor 66 returns back to step 252 and periodically repeats the step of determining whether power is received (step 252) as shown in FIG. 9. In another embodiment, a switch or relay directly provides a signal to the electronic processor 66 when power is received.

When the handpiece 20 is receiving power, the electronic processor 66 operates to determine or sense one or more of temperature data from the temperature sensor 40, force or axial load from the force sensor 80, vibration data from the vibration sensor, and acoustic data from the microphone 90 (step 256). Further, in one embodiment, the operation includes sensing or determining motor power data from the motor power sensor 84, along with motor position data, and motor rotational speed data (step 256). Motor power data from the motor power sensor 84 includes sensing at least one of current and voltage of the electric motor for driving the handpiece 20.

The electronic processor 66 provides time stamps or marks for the data obtained to log the time and sensor data values in the handpiece memory 70 (step 260). At a later occurrence, both the time stamps and data values for the logged data are available for calculations and comparisons. In other embodiments, additional temperature data for bearings and drive shafts of the handpiece 20 is also obtained and stored in the handpiece memory 70 with a time stamp. Thus, the handpiece memory 70 stores motor operating data, force or load data for an axial force applied to the handpiece 20, vibration data that is at least one of acceleration and deceleration sensed by a vibration sensor 88 and/or sound vibrations sensed by a microphone 90 for future analysis.

The sequence of steps shown in FIG. 9 is repeated to obtain an operating or historical usage data of the handpiece 20. In this embodiment, historical data data for the handpiece 20 is obtained that includes operating time as well as the specific properties that are measured. As a result of the processing performed by the electronic processor 66, historical usage data for the various properties of the handpiece 20 is obtained and stored thereon for later evaluation.

While sensing temperature, vibration, force, and power provided by or from an electric motor and handpiece components is disclosed in FIG. 9, other properties, such as motor torque and rotational shaft speed (magnet and Hall effect sensors) are determined and stored in one embodiment. In another embodiment, the motor that powers the handpiece 20 is a pneumatic motor. Power of the pneumatic motor is determined with a force and/or pressure sensor, along with a rotation speed sensor for rotation of the drive shaft of the handpiece 20.

Figure 10:
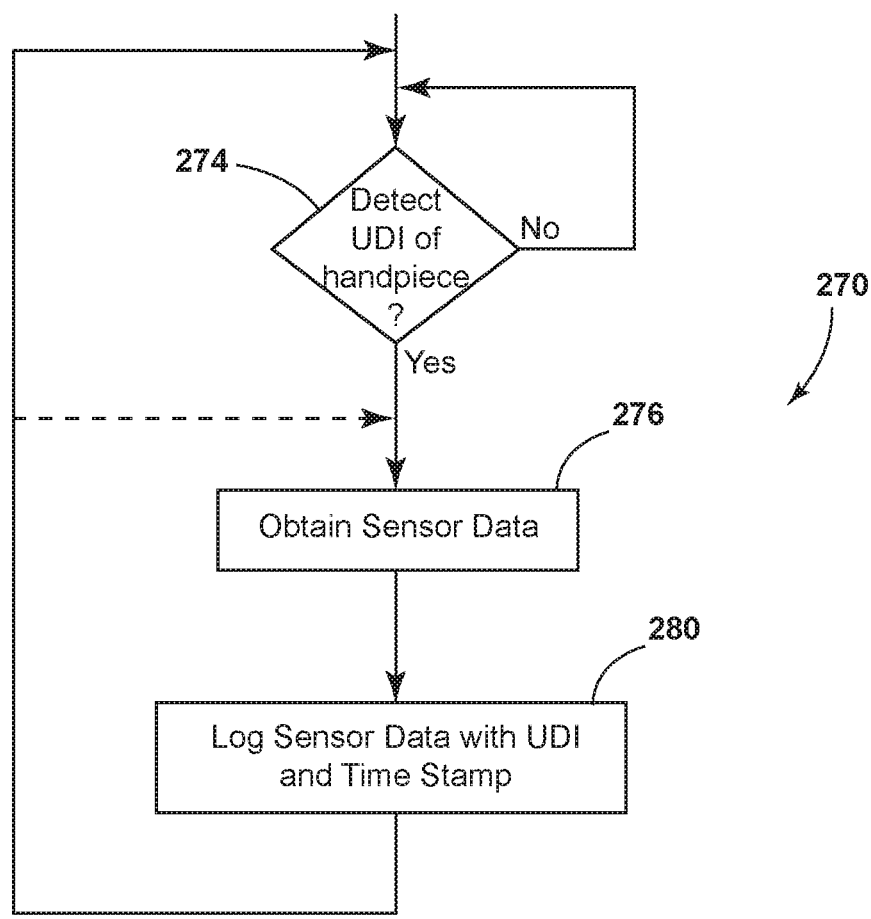
FIG. 10 illustrates a flow chart for operation of the sensing arrangement shown in FIG. 3.

FIG. 10 illustrates a flow chart of a method 270 for operating the system during a procedure, including sensors 40, 88, 90, and the electronic processor 92 shown in FIG. 3. The electronic processor 92 determines the presence of and the identity of a handpiece 20 and operating properties thereof. In one example, the electronic processor 92 operates a short range RFID transceiver 99 to sense the presence of a unique identifier for a UDI 44 of a nearby handpiece 20 (step 274). If no UDI is received, the electronic processor 92 periodically returns to retry detecting of the UDI 44. When the electronic processor 92 determines a unique identifier for the handpiece 20 is provided from the short range RFID transceiver 99 (decision step 274), the method advances to operate the sensors 40, 88, 90 to sense and provide sensor data for the handpiece 20 (step 276) in the event the handpiece 20 is operating. When the handpiece 20 is not operating, the electronic processor 92 reads usage data from the memory 70 of the handpiece (step 276). While a laser vibrometer 89, a thermal imaging sensor 40, and a microphone 90 are illustrated, additional sensors are contemplated. For example, an ambient temperature sensor and a humidity sensor are provided to provide temperature and humidity data for a room that includes a treatment unit.

The method then assigns the unique device identifier and a time stamp to the sensed data to log the data (step 280). Thereafter, the identity of the handpiece 20 is reconfirmed and data is logged so long as the handpiece 20 is identified. While FIG. 10 shows re-identifying the handpiece for every iteration of the method, in one embodiment, after initially identifying the handpiece 20, the electronic processor 92 executes the iteration from 10 to 500 times before again identifying the handpiece 20 (see broken line with arrow). Thus, more efficient executing of the method shown in FIG. 10 is provided.

Upon completion of the logging of sensor data as shown in FIG. 10, the electronic processor 92 has logged the sensor data into the memory 94. Thereafter, the electronic processor 92 provides the sensor data to the memory of the handpiece 20 via the short range RFID transceiver 99. Alternatively, or in addition, the electronic processor 92 provides the usage data over the local wireless transceiver 96 and via a network access point 200 to a cloud computer 220, other computer, or remote memory storage device for later use.

Reading Operation of Dental Handpiece Maintenance System

The dental handpiece maintenance system 100 shown in FIG. 3 performs maintenance for the handpiece 20, including applying oil and cleaning a used handpiece. In addition, in some embodiments, the dental handpiece maintenance system 100 is configured to read sensor data from the memory 70 of the handpiece 20.

After a dental procedure, an operator detaches a handpiece 20 from the coupler 50 and mounts or secures the handpiece used in the procedure onto a maintenance coupling 110 of the dental handpiece maintenance system 100. The operator closes the entrance 114 to seal the handpiece 20 in a chamber and actuates a cleaning operation wherein a cleaning fluid is provided to the handpiece for a washing cycle. In one embodiment, the washing cycle includes a rinse event. The washing cycle is one type of maintenance cycle for the dental handpiece maintenance system 100. In one embodiment, thereafter oil is sprayed on the handpiece 20 followed by a purging with compressed air applied to distribute the lubricant, blow out excess lubricant and debris in the handpiece. Some embodiments include a further sterilization cycle. Thus, the handpiece 20 is cleaned by the dental handpiece maintenance system 100. The electronic processor 66, the memory 70, and other components of the handpiece 20 are provided with a waterproof seal by a sealing coating, an enclosure or other layer(s) implemented using know arrangements or techniques to prevent damage thereto during washing, purging with compressed air, and lubricating of the handpiece. In one embodiment, the dental handpiece maintenance system 100 selectively operates for one or more from a group of maintenance cycles that includes a washing cycle, a lubrication cycle, and a sterilization cycle.

Figure 11:
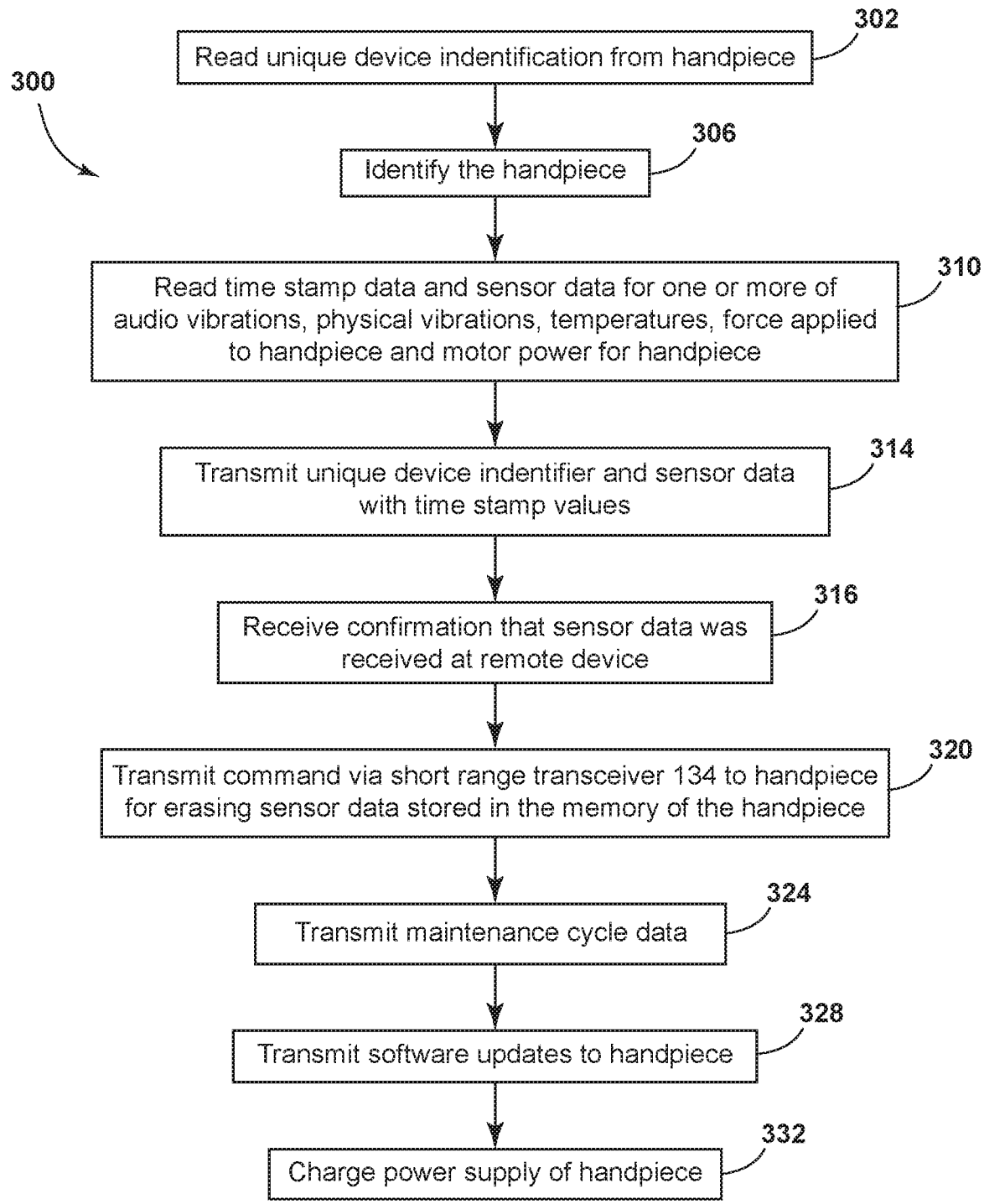
FIG. 11 illustrates a flow chart for operation of the dental handpiece maintenance system.

In addition to controlling washing and lubricating, the electronic processor 126 and the short range transceiver 134 of the dental handpiece maintenance system 100 nearest the handpiece 20 as shown in FIG. 5, operate as shown in the flow chart 300 of FIG. 11. In the method shown in FIG. 11, the short range transceiver 134 of the dental handpiece maintenance system 100 reads a unique device identifier 44 from the nearby handpiece 20 (step 302) and provides the device identifier to the electronic processor 126 of the dental handpiece maintenance system 100. In one embodiment, the electronic processor 126 executes a program to identify the handpiece 20 (step 306) from UDI data or information. Thereafter, the electronic processor 126 utilizes the short range transceiver 134 to communicate via the short range transceiver 74 with the electronic processor 66 of the identified handpiece 20 to obtain time stamp data and one or more of audio vibration data, physical vibration data, temperature data, handpiece force data, and power applied or motor operating data (step 310) from the memory 70 of the handpiece. The sensor data is temporarily stored in the memory 130 of the dental handpiece maintenance system 100 in one embodiment.

Thereafter, as shown in FIG. 11, the electronic processor 126 executes a program or is configured to transmit the unique device identifier for the handpiece 20, along with the various types of sensor data with time stamp values, via a local transceiver 135 (step 314) or via a hard wired connection from the output port 136, to a remote electronic controller, such as a cloud computer 220 or other device. Upon receiving a return confirmation that the sensor data was received at the remote electronic controller (step 316), the electronic processor 126 is configured to transmit instructions, such as a request or a command via the short range transceiver 134 to the electronic processor 66 of the handpiece 20 to erase the sensor data stored in the memory 70 thereof (step 320). Thereafter, the electronic processor 66 erases the sensor data stored in the memory 70 or simply classifies the memory as available for storage to write over the sensor data stored therein. Therefore, additional memory is re-available in the handpiece 20 to store sensor data during additional usage data of the handpiece.

In an addition, during washing and lubrication cycles and/or a sterilization cycle by the dental handpiece maintenance system 100, cycle data is collected and read from sensors on the handpiece 20 or sensed by the temperature sensor 140 and the vibrometer 144. The maintenance cycle data is transmitted by the electronic processor 126 via the local transceiver 135 or the hard wired output port 136 through a network access point 200 to the cloud computer 220 or other computer device for storage as maintenance cycle or history data for the given identified handpiece 20 (step 324) as shown in FIG. 11. Thus, in one embodiment, the dental handpiece maintenance system 100 operates for washing, lubricating and sterilizing the handpiece 20.

In some instances, the dental handpiece maintenance system 100 receives software updates for the handpiece 20 from a cloud computer 220 or other location. Then the short range transceiver 134 of the dental handpiece maintenance system 100 transmits the software updates to the short range transceiver 74 of the handpiece 20 for storage in the handpiece memory 70 (step 328) and for execution by the electronic processor 66.

In one embodiment, the power supply 78 of the handpiece 20 is recharged by power provided by the dental handpiece maintenance system 100 (step 332) either wirelessly or by a wired connection.

The steps illustrated in FIG. 11 can be provided in a different order. The steps shown can also be performed simultaneously. Further, while the short range transceiver 134 for the dental handpiece maintenance system 100 and the short range transceiver 74 for the handpiece 20 are shown for communication purposes. A port and pin connection is also contemplated, wherein the maintenance coupling 110 includes one or more pins to both support the handpiece 20 and electrically communicate with the memory 70 and the electronic processor 66 via the output port 76 of the handpiece.

Reading Operation of Delivery Unit

The delivery unit 170 shown in FIGS. 6 and 7 includes an electronic controller 180 and short range transceivers 190. The short range transceivers 190 are located near or adjacent handpieces 20, when the handpieces are returned to a tray 174 of the delivery unit 170 after usage.

The reading operation of the delivery unit 170 shown in FIG. 7 is essentially the same as the reading operation of for sensor data by the dental handpiece maintenance system 100. Short range transceivers 190 communicate with an adjacent or nearby handpieces 20. The sensor data in the memory 70 of the handpiece 20 is transmitted by the short range transceiver 74 thereof and via the short range transceiver 190 to an electronic processor 194 of the delivery unit 170. The electronic processor 194 stores the sensor data in memory 196 and/or transmits the data by a local transceiver 198 or an input/output port 199 via the network access point 200 to a remote electronic controller or other device, such as the cloud computer 220. Upon confirmation of successful transmission to a remote electronic controller or cloud computer 220, the electronic controller 180 shown in FIG. 7 transmits an erase command via the short range transceiver 190 to the handpiece 20. Therefore, the electronic controller 180 senses that the handpieces 20 are in communication with the delivery unit 170 and operates in essentially the same manner as shown in the flow chart 300 of FIG. 11 for the dental handpiece maintenance system 100.

The dental handpiece maintenance system 100 and the delivery unit 170 are both considered a communication system for communication with the handpiece 20. The tray 174 of the delivery unit 170 acts as a docking station for receiving one or more of the handpieces 20. A short range transceiver 190 of the delivery unit 170 is configured to read the data stored in the handpiece memory 70. In some instances, the tray 174 includes a battery charging arrangement to wirelessly or by a wired connection charge the power supply 78 of the handpiece 20.

Predictive Maintenance

Predictive maintenance for the handpiece 20 is determined by one or more of the dental handpiece maintenance system 100, the delivery unit 170, the portable universal controller 210, the computer work station 214, and/or the cloud computer 220 (hereinafter). More specifically, sensor data for the handpiece 20 is loaded into one or more of the above listed computing systems, units, and computers. The sensor data from the sensors includes corresponding date stamps and thus represents usage data for the handpiece 20. Additional sensor data not provided by the handpiece 20 is also obtained in some embodiments and considered handpiece data. For instance, ambient temperature and humidity data not read from the handpiece 20, but sensed near the handpiece is considered handpiece data. Further, real time data, including ambient temperature, along with motor operating data for the handpiece is considered handpiece data.

Figure 12:
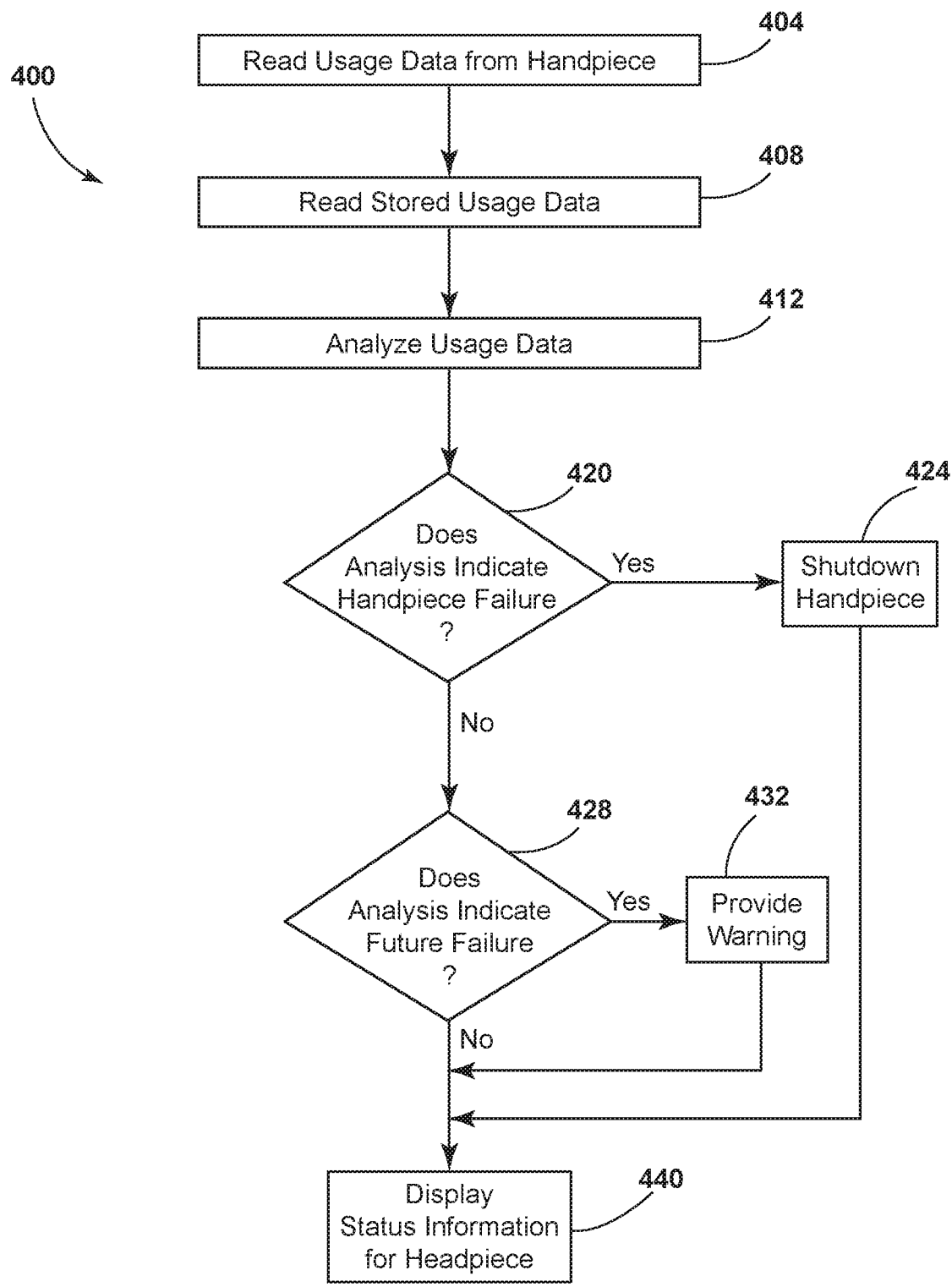
FIG. 12 illustrates a flow chart for execution of predictive maintenance.

In one embodiment, predictive maintenance is provided by the electronic controller 180 of the delivery unit 170 when the handpiece 20 has been utilized in a procedure and placed on a tray 174 near a short range transceiver 190 of the delivery unit. In the method shown in the flow chart 400 of FIG. 12, the short range transceiver 190 reads usage data, timestamp data, and unique identifier UDI data from the handpiece 20 and provides same to the electronic controller 180 (step 404) in a manner similar to the manner discussed above and shown in FIGS. 10 and 11.

Then, the electronic controller 180 searches one or more of the cloud computer 220, a data logging equipment (not shown) or other computer having memory to locate and receive additional usage data for the handpiece 20 that was previously stored (step 408). The additional usage data for the handpiece 20 includes motor operating data for the motor that drives or has driven the handpiece. In one embodiment, the additional handpiece data includes humidity and ambient temperature for a room that contains a treatment unit 160 including the handpiece 20.

The electronic controller 180 then analyzes the sensor data for the handpiece 20 from the various sources (step 412). In one embodiment, the cumulative wear on the handpiece 20 is determined. The usage data that is analyzed includes handpiece operating speeds, operating times, usage time, along with ambient air temperature, and humidity conditions in one embodiment. Power consumption, torque, applied loads (radial and axial) for a motor driving the handpiece 20 are included for analysis in another embodiment. Multiple temperature sensors 40 are provided for multiple bearings of the handpiece in one embodiment, and the analysis includes determining rate of temperature increase and thermal time constants for the handpiece 20. In one embodiment, the maintenance cycle data is also evaluated to determine the condition of the handpiece 20.

The electronic controller 180 compares the analyzed data with failure data for the particular model of the handpiece 20 (step 420). When the analyzed data indicates or predicts failure or imminent failure, the electronic controller 180 operating for shutting down or disabling operation of the handpiece (step 424).

When the analyzed data does not indicate failure (step 420), the electronic controller compares the analyzed data with future failure data for the particular handpiece (step 428). When the analyzed data indicates future failure (step 428), the electronic controller 180 provides a preventive maintenance warning (step 432) on the display 188 that the handpiece 20 will need replacement or repair.

When the analyzed data does not indicate future failure (step 428), the status of the handpiece is provided on the display 188 (step 440). In the instances of handpiece shutdown (step 424) and providing a preventive maintenance warning (step 432), thereafter, the flow chart 400 advances to step 440 and also provides a display status of the handpiece 20.

Specific examples of handpiece data analysis are discussed as follows. In one embodiment, the sensor data includes temperature data from a second end of the handpiece 20. The previous temperature data is compared with the recent temperature data of the handpiece 20 by an electronic processor to determine change of temperature for the temperature sensor 40. When temperature data and/or the change of temperature is beyond or exceeds preselected values, a preventive maintenance warning as in step 432 or shutdown or disabling of operation of the handpiece 20 as shown in step 424 of FIG. 12 occurs.

In another embodiment, the sensor data for predictive maintenance analysis includes physical vibration data obtained by an accelerometer secured to the handpiece 20 or obtained by a laser vibrometer 89 mounted to the treatment unit 160, and temperature data from temperature sensors disposed near the bearings of the handpiece, along with handpiece operating speeds, handpiece operating times, ambient air temperature, and humidity conditions. For the analysis step, an electronic processor or controller is configured to determine bearing/shaft condition of the handpiece 20, and provide a preventive maintenance indication when the bearing/shaft condition indicates an approaching failure for the handpiece. This data, and especially the temperature data, is executed by the processor through a series of thermal equations that calculate and obtain heat generating rates of the bearings/handpiece 20 and/or thermal time constants. The method sends this data to cloud storage or compares the heat generating rates locally with the history of previously calculated results for the handpiece 20. When an unacceptable variance from the calculated heat generating rates and/or the average of the last several calculated rate results for the same handpiece 20 is obtained, the method provides an indication or preventive maintenance warning that recommends handpiece maintenance for the handpiece or a particular component thereof.

In one embodiment, sensor data from at least one of a group consisting of a handpiece memory 70 of a handpiece 20 and a motor for driving the handpiece is analyzed to determine predictive maintenance conditions for the handpiece of the treatment unit 160 and provide the preventive maintenance indications for multiple conditions.

In another embodiment, the predictive maintenance is provided by the portable universal controller 210. For instance, the portable universal controller 210 is operable to provide a preventive maintenance warning when the sensor data indicates that the temperature exceeds a preselected value. The temperature, change of temperature, vibration, motor usage, and other conditions are conditions that are analyzed to obtain predictive maintenance conditions that correspond to a predictive maintenance warning or indication for the handpiece 20.

Further approaches to determining predictive maintenance conditions are set forth in U.S. Ser. No. 15/494,096 filed Apr. 21, 2017 and titled "Predictive Maintenance System and Method for 1-Wire Handpiece," the disclosure of which is hereby incorporated by reference herein.

Graphical User Interface

Figure 13:
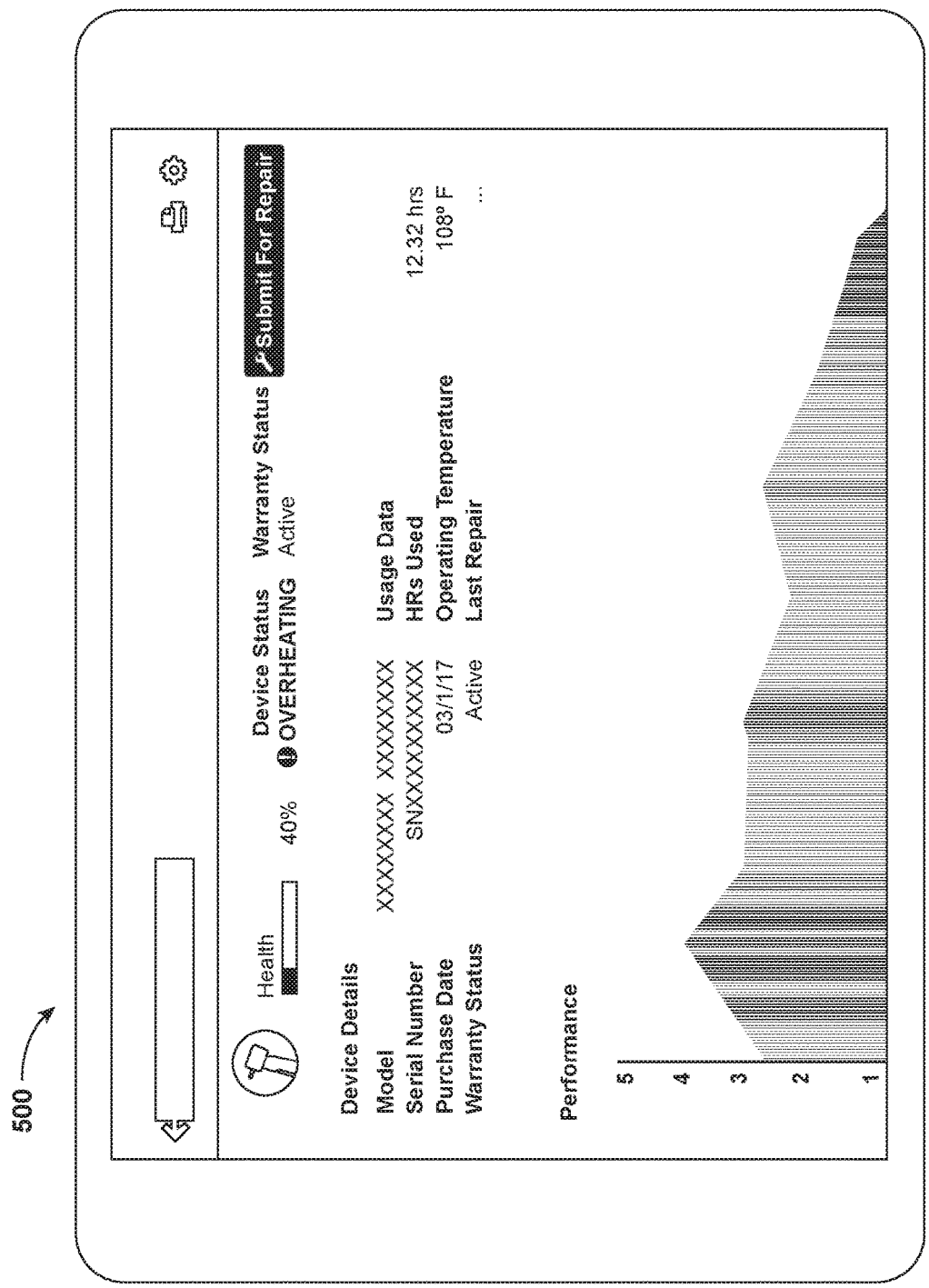
FIG. 13 illustrates a graphical user interface for a display of a delivery unit.

FIG. 13 illustrates a graphical user interface (GUI) 500 displays, among other things, conditions of a handpiece 20. The GUI 500 shows the model number and a unique serial number for the handpiece 20. The GUI 500 also shows a handpiece status of "OVERHEATING" and a health status of 40%. Further, the GUI 500 shows a total hours used (in one example, 12.32 hours) and an operating temperature (in one example, 108 degrees Fahrenheit (F)). Further, a graphical performance display of historical performance of the handpiece 20 over time is displayed as a graph at the lower part of the GUI 500. The graphical performance display has a scale, which is the example provided is from 1 to 5 with 5 being the highest or optimal performance. The overheating condition results in a lower value displayed on the right end of the bar graph. The bar graph includes various colors (not shown) relating to the performance thereof. The condition shown in FIG. 13 corresponds to an overheating warning or warning only stage as discussed with above respect to FIG. 12. Further, if the operating temperature of the handpiece 20 increases to a severe level, the increased severity of the temperature maintenance condition results in the shutdown of the handpiece and the GUI 500 will display information indicating the handpiece 20 is shutting down and may include an explanation why, Tool Wear Another embodiment includes determining or sensing vibration data with the vibration sensor 88 provided on the handpiece 20 as shown in FIG. 2. The vibration data is processed and a preventative maintenance indication or preventative maintenance warning is provided when the vibration data values indicating a wear condition for a cutting tool 34 secured to the handpiece 20. In one embodiment, the type of cutting tool 34 mounted to the handpiece 20 is stored in cloud computer 220, along with the historical usage data thereof. Further, the type of operation procedure, including the type of tissue to be cut, is enterable by an operator. The system processes the vibration data value based on the additional information provided. In this embodiment, tool wear for the tool 34 secured to the handpiece 20 is determined.

FIGS. 1-3 show a temperature sensor or thermal sensor 40. Additional temperatures sensors for the drive assembly bearings of the handpiece 20 are contemplated. The temperature sensors are not limited to the bearings, but may also include components in contact with the bearing in which heat may transfer through, such as a bearing holding assembly, a handpiece body or any one of the internal shafts. The temperature of these components may be measured by means of an internal temperature sensor disposed in the handpiece 20 or an external temperature sensor.

In one embodiment, a timestamp or time marker is digital data providing a date, hour, minute, and milliseconds that a sensed value was obtained. The timestamp is associated with sensor data for a particular sensor, such as a temperature sensor, humidity sensor, a vibration sensor, and a motor position sensor. In other embodiments, the time marker is also associated with handpiece motor conditions.

The use of an electronic processor 66 and a RFID tag for the handpiece 20 is discussed herein. The handpiece 20 can be an active RFID device and the sensors may include humidity or moisture, along with additional temperature sensors as set forth above.

In one embodiment, the handpiece 20 is a dental handpiece, the treatment unit 160 is a dental treatment unit, and the delivery unit 170 is a dental delivery unit.

Dental Handpiece Maintenance System with Diagnostic Mode

Figure 14:
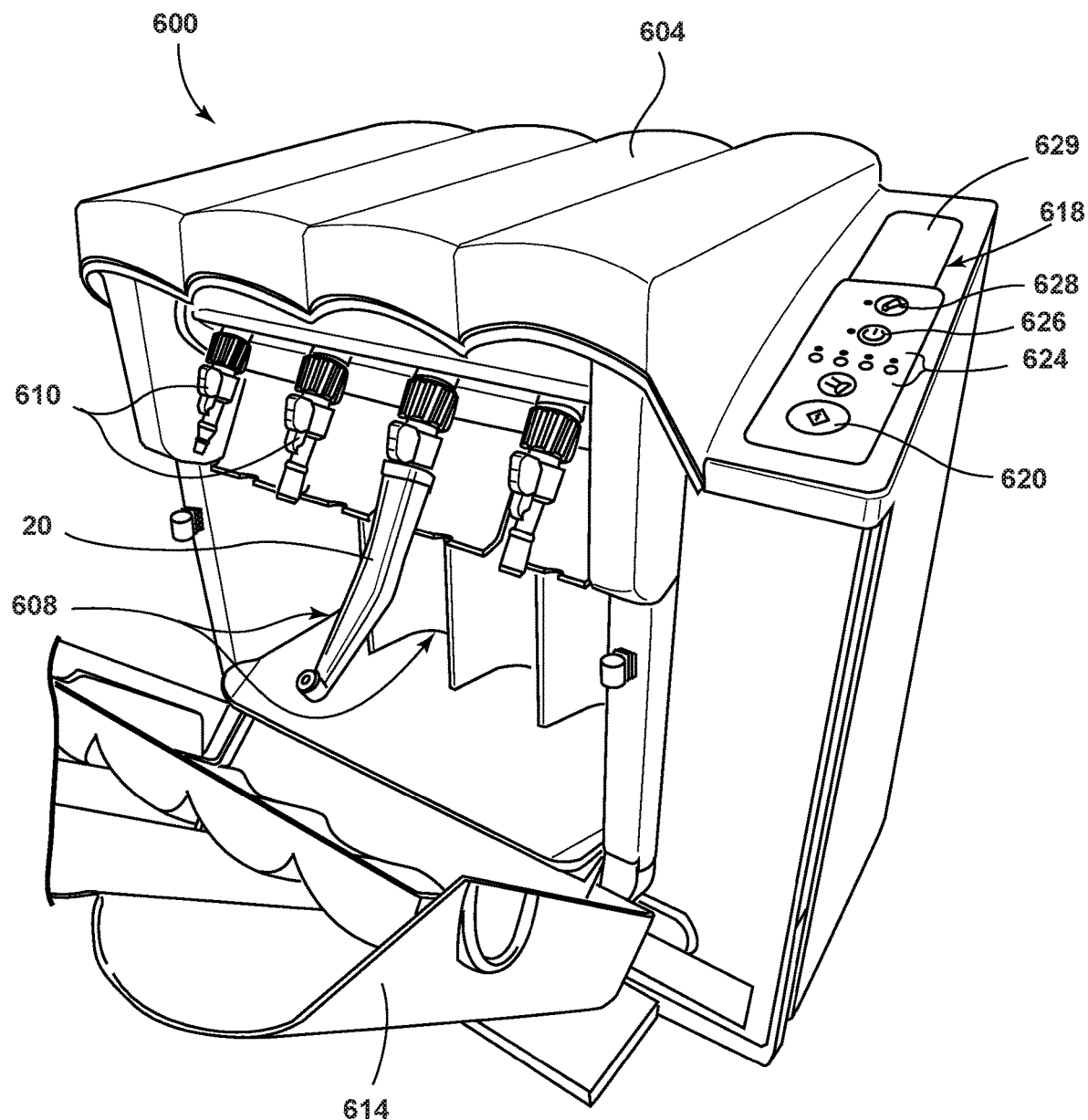
FIG. 14 illustrates a perspective view of a dental handpiece maintenance system that has a diagnostic cycle.

FIG. 14 illustrates a dental handpiece maintenance system 600 that includes a diagnostic cycle or test mode. The dental handpiece maintenance system 600 includes a housing 604 and a plurality of chambers 608 having maintenance couplings 610 or service couplings for receiving a dental handpiece 20 in a similar manner as shown in the embodiment of FIG. 4. The handpiece 20 shown in FIG. 14 is secured to a maintenance coupling 610. An entrance 614 provides access to the chambers 608 to enable placement of the handpieces 20 in the respective chambers for treatment. A display 618 displays the status of the dental handpiece maintenance system 600 and additional information. In one embodiment, the display 618 is an input/output interface that includes an on/off button 620, light indicators 624 for individual chambers 608, a spray can control indicator 626, a spray can control 628, and a graphical user interface (GUI) 629. In another embodiment, a display as shown in FIG. 4 replaces the arrangement shown in FIG. 14. In one embodiment, the GUI 629 enables programming of lubricating and purging cycles, along with diagnostic or testing cycles. In another embodiment, the entire display 618 is a GUI 629 that operates as a touchscreen.

Figure 15:
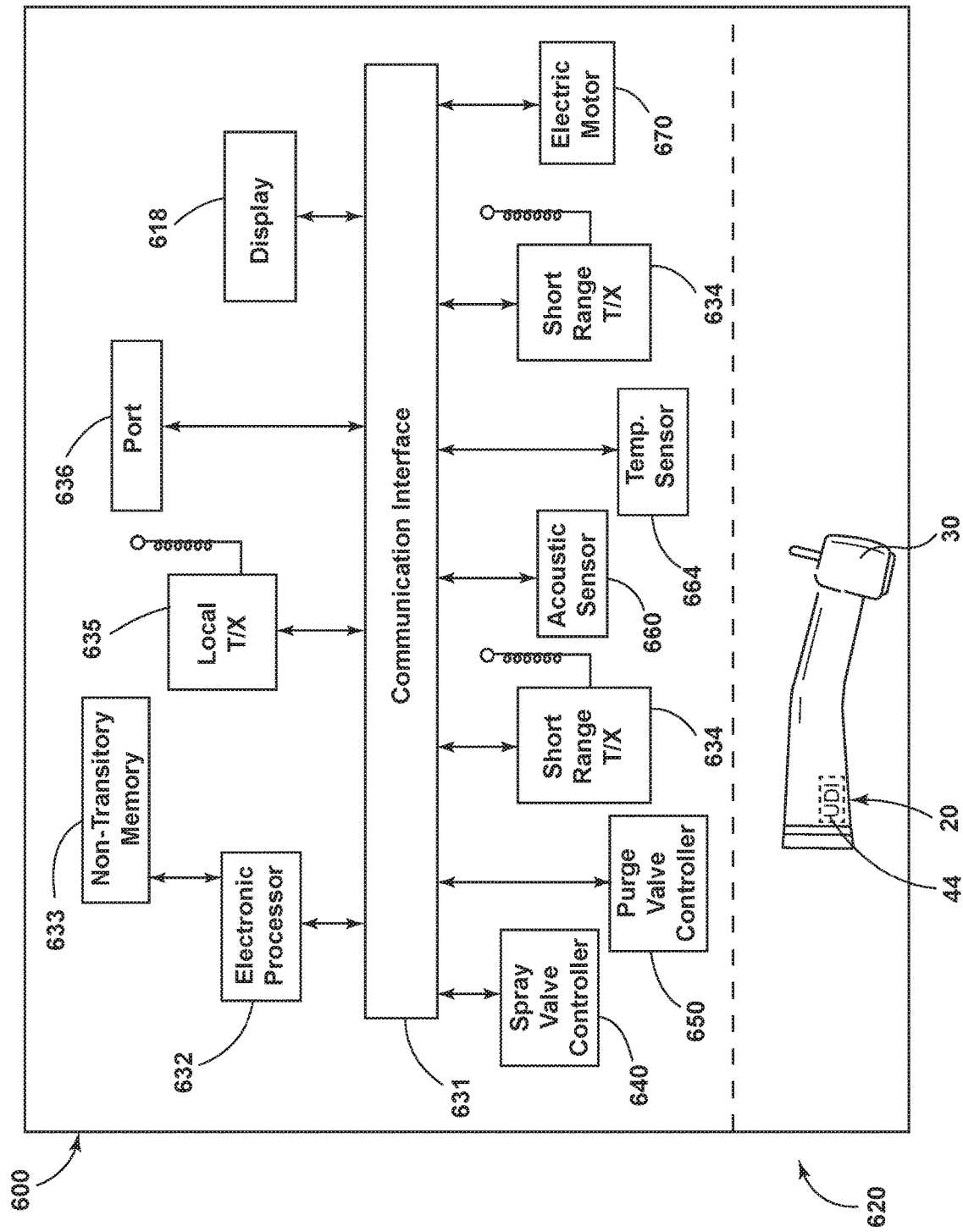
FIG. 15 illustrates a block diagram of the dental handpiece maintenance system of FIG. 14.

The block diagram 630 shown in FIG. 15 of the dental handpiece maintenance system 600 includes a communication interface 631, an electronic processor 632, and a memory 633 in communication with the electronic processor. Further, the block diagram 630 includes short range transceivers 634, a local transceiver 635, a port 636, and the display 618 electrically connected to the communication interface 631. These components operate in a similar manner discussed above in the embodiment shown in FIG. 5, except as discussed below.

FIG. 15 shows a spray valve controller 640 and a purge valve controller 650 of the dental handpiece maintenance system 600. The spray valve controller 640 receives signals or commands from the electronic processor 632 to control the spray of cleaning agents or lubricants into the handpiece 20 mounted to a maintenance coupling 610. Likewise, the purge valve controller 650 receives signals or commands from the electronic processor 632 to control the purging of the lubricants from the handpiece 20 with high pressure air applied thereto via the maintenance coupling 610. An air pressure source (not shown) includes a high pressure air carrying line that connects to an air input on the housing 604 of the dental handpiece maintenance system 600. While a single spray valve controller 640 and a single purge valve controller 650 are illustrated, these controllers are arranged to control multiple valves, if necessary, to selectively provide lubricant and to selectively purge each of the respective maintenance couplings 610 by providing bursts of air. A spray can (not shown) is disposed in the dental handpiece maintenance system 600 to provide cleaning agents or lubricants to the handpieces 20. Additional components for applying the cleaning agents or lubricants to the handpieces 20, and otherwise treating the handpieces 20, are not related to predictive maintenance or to the diagnostic method, and thus not further described herein.

FIG. 15 also shows an acoustic sensor 660 that is located in the chamber 608, along with a temperature sensor 664 located in the chamber 608. While a single acoustic sensor 660 and a single temperature sensor 664 are shown, in another embodiment, individual acoustic sensors 660 and temperature sensors 664 are provided for each of the four chambers 608 shown for receiving four handpieces 20. In one embodiment, the temperature sensor 664 is an optical temperature sensor for sensing the temperature of the body of the handpiece 20. In another embodiment, a vibration sensor is an accelerometer to sense vibration. The accelerometer and the temperature sensor 664 are located inside the chamber 608 of the dental handpiece maintenance system 600.

Figure 16:
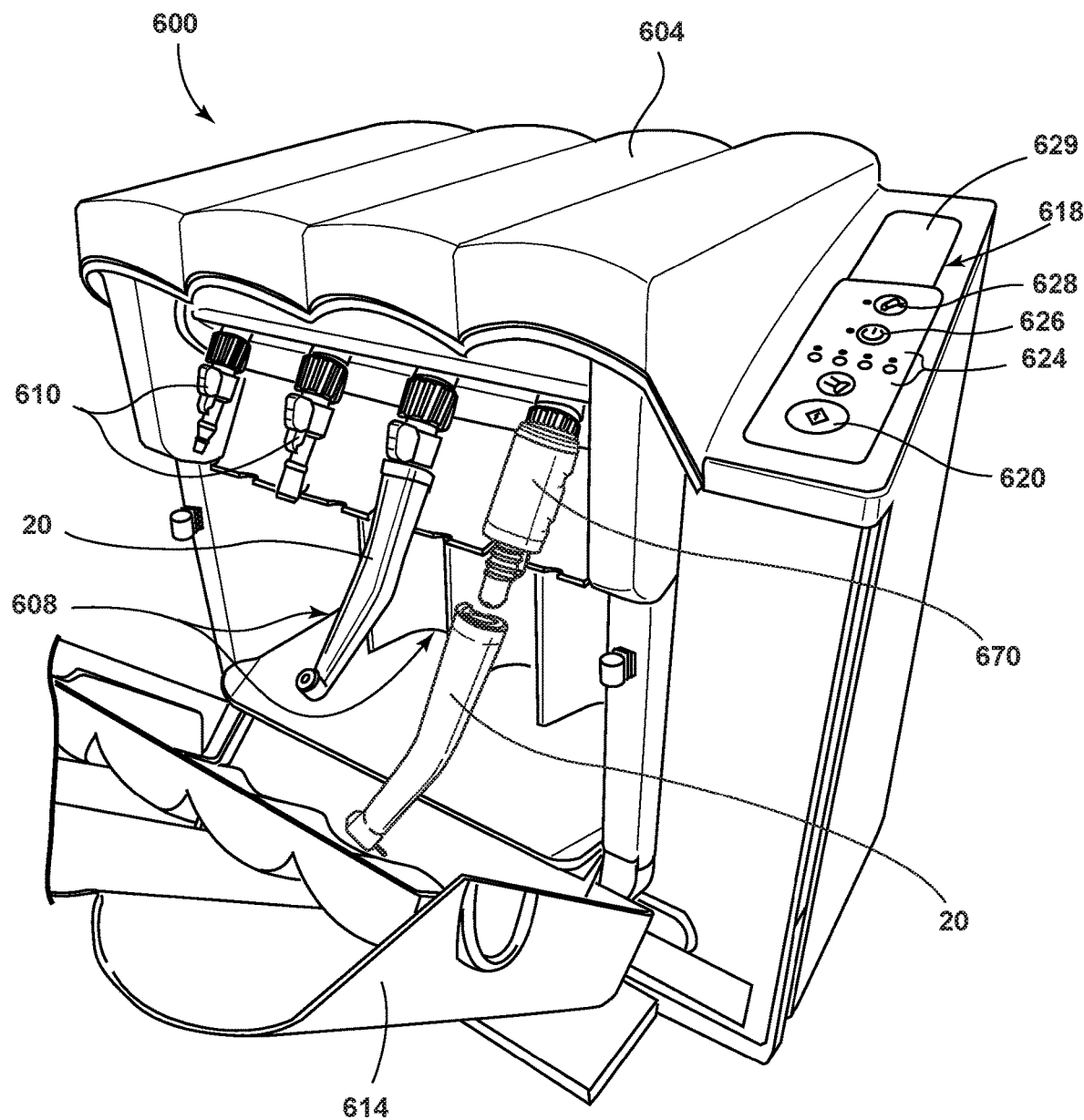
FIG. 16 illustrates a perspective view of a dental handpiece maintenance system that includes an electric motor.

Further, FIG. 15 shows an electric motor 670 provided as a maintenance coupling for the dental handpiece maintenance system 600 for powering or driving a handpiece in a diagnostic cycle in one embodiment. FIG. 16 shows the electric motor 670 provided in the chamber 608 of the dental handpiece maintenance system 600 as a maintenance coupling for joining with a handpiece 20. The handpiece 20 shown is FIG. 16 is a legacy handpiece that does not include a unique device identifier 44 and/or any sensors.

Figure 17:
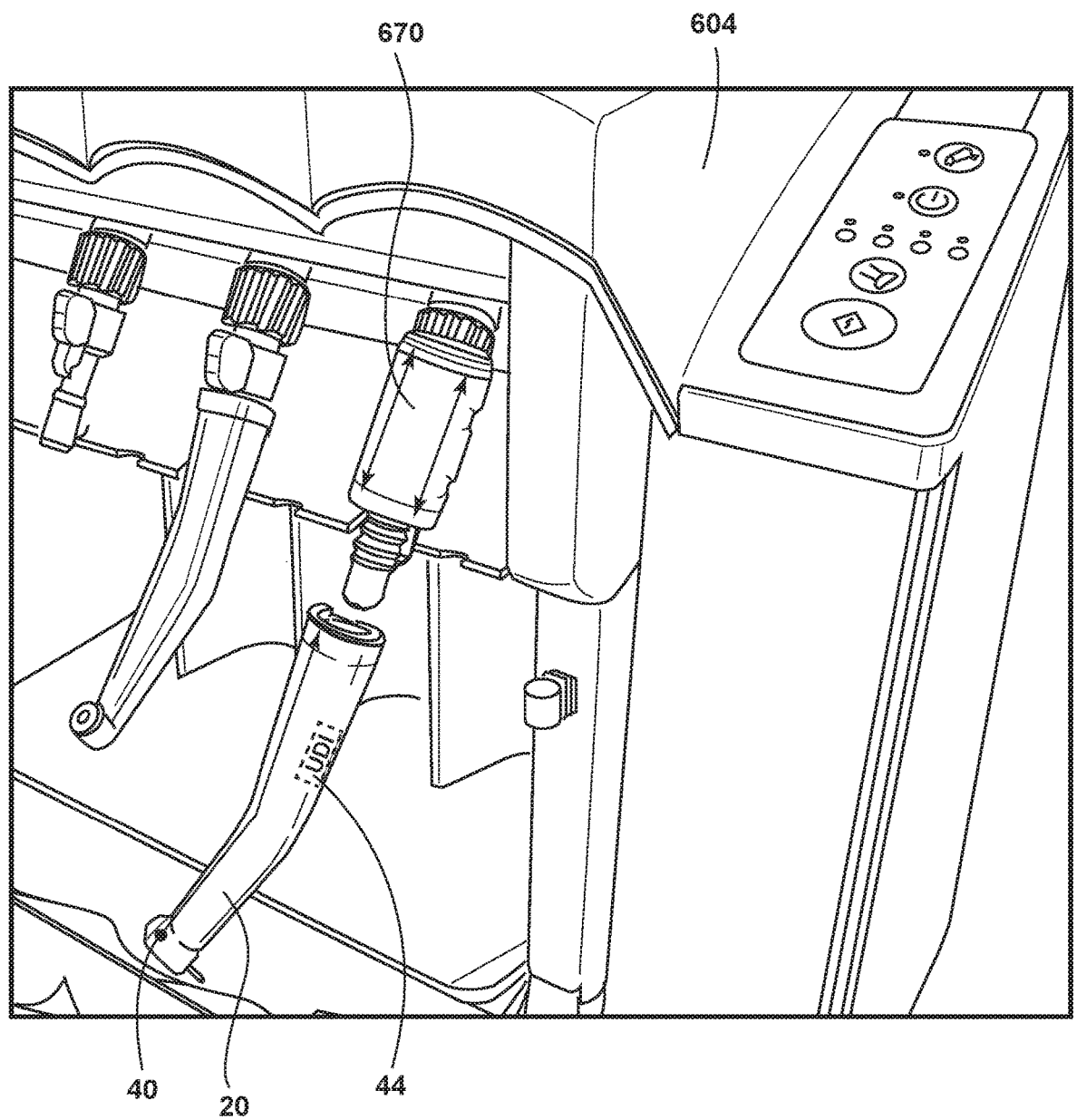
FIG. 17 illustrates a perspective of a dental handpiece maintenance system that includes an electric motor with communication lines for a sensor on the handpiece.

FIG. 17 shows a close up view of a one-wire handpiece 20 to be installed on an electric motor 670 having data communication lines disposed therein. Further, the handpiece 20 includes a unique device identifier 44 and a thermal sensor 40. The handpiece 20 shown in FIG. 17, however, does not include an electronic processor or memory as shown in the embodiment of FIG. 2. Instead, in the handpiece 20 shown in FIG. 17 a wired electrical connection exists between the thermal sensor 40 and the electronic processor 632 of the dental handpiece maintenance system 600. The wired electrical connection includes a data communication line of the electric motor 670. In one embodiment, the electric motor 670 includes an air flow path (not shown) therein for applying lubricant to the handpiece 20 or for purging the handpiece with compressed air.

Figure 18:
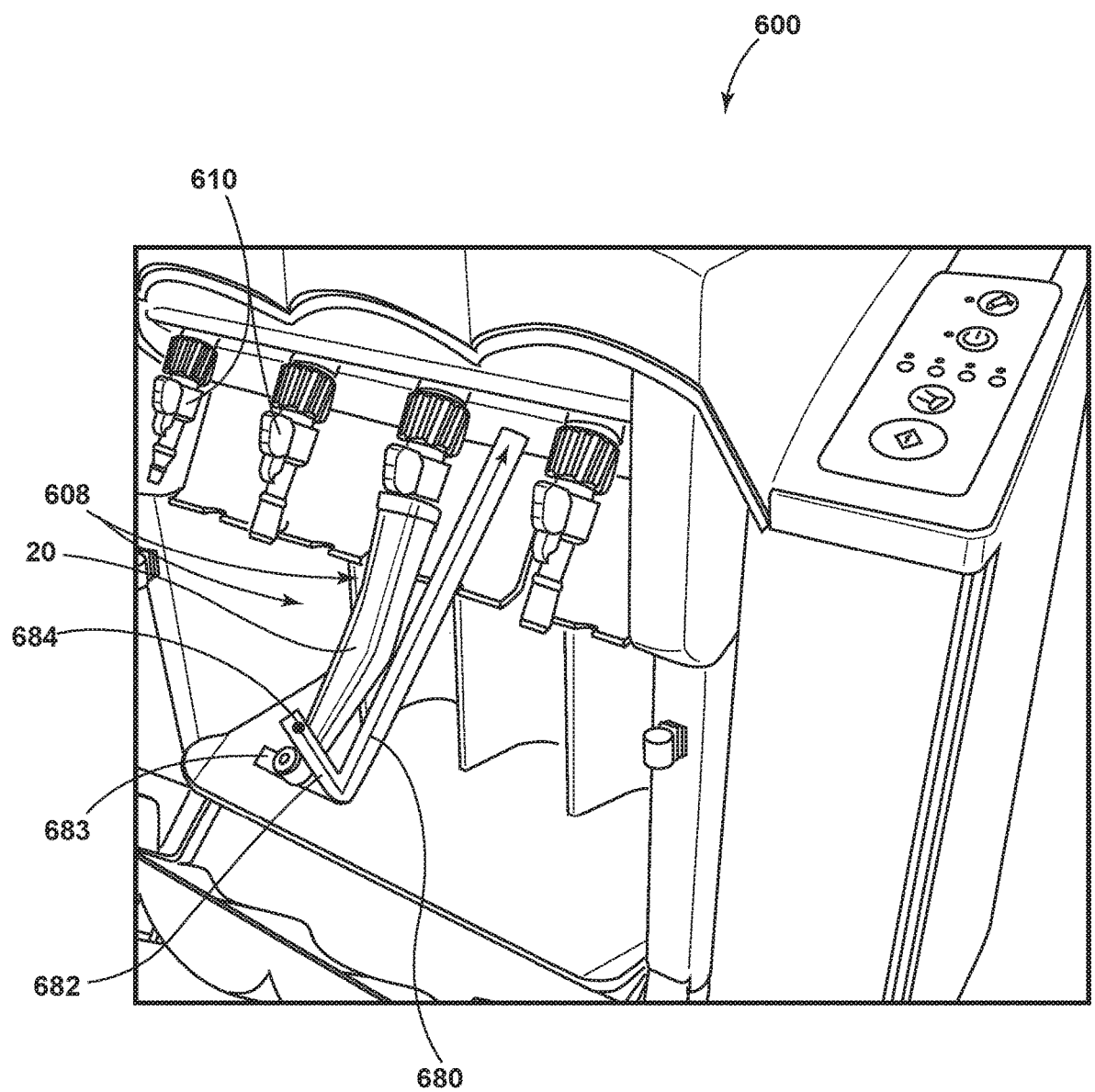
FIG. 18 illustrates a perspective of a dental handpiece maintenance system that includes a support arm to grip and sense the handpiece.

FIG. 18 shows another embodiment of the dental handpiece maintenance system 600 that includes a handpiece 20 secured at a first end to the maintenance coupling 610. Further, FIG. 18 shows a support arm 680 that is secured at a first end to a wall of the chamber 608 or is otherwise mounted to the dental handpiece maintenance system 600 within the chamber. The second end of the support arm 680 has forks 682, 683 for receiving the second end of the handpiece 20 as shown in FIG. 18. In one embodiment, the forks 682, 683 have properties and dimensions to fixedly maintain the position of the handpiece 20. At least one of the forks 682 includes one or more sensors 684. The sensors 684 are connected by data communication lines through the body of the support arm 680 and via the port 636 to the electronic processor 632 of the dental handpiece maintenance system 600. The sensors 684 provided with the support arm 680 are an accelerometer and/or a temperature sensor in one embodiment. The temperature sensor is an optical temperature sensor to sense the temperature of the body of the handpiece 20. Thus, the support arm 680 includes an accelerometer to sense vibration of the handpiece 20, a temperature sensor to sense temperature of the handpiece 20, or both.

The dental handpiece maintenance system 600 is configured to communicate with the various systems and controllers shown in FIG. 8, including a portable universal controller 210, a computer work station 214, and/or a cloud computer 220 via a network access point 200.

Operation of the Handpiece Maintenance System with Diagnostic Mode for Pneumatic Driven Handpiece The dental handpiece maintenance system 600 shown in FIGS. 14 and 15 performs maintenance for the handpiece 20, including applying oil and cleaning as follows. An operator attaches or secures a handpiece 20 used in a procedure onto a maintenance coupling 610 of the dental handpiece maintenance system 600. The operator operates the entrance 614 to seal the handpiece 20 in the chamber 608. The handpiece 20 shown in FIG. 15 is pneumatically driven.

Figure 19:
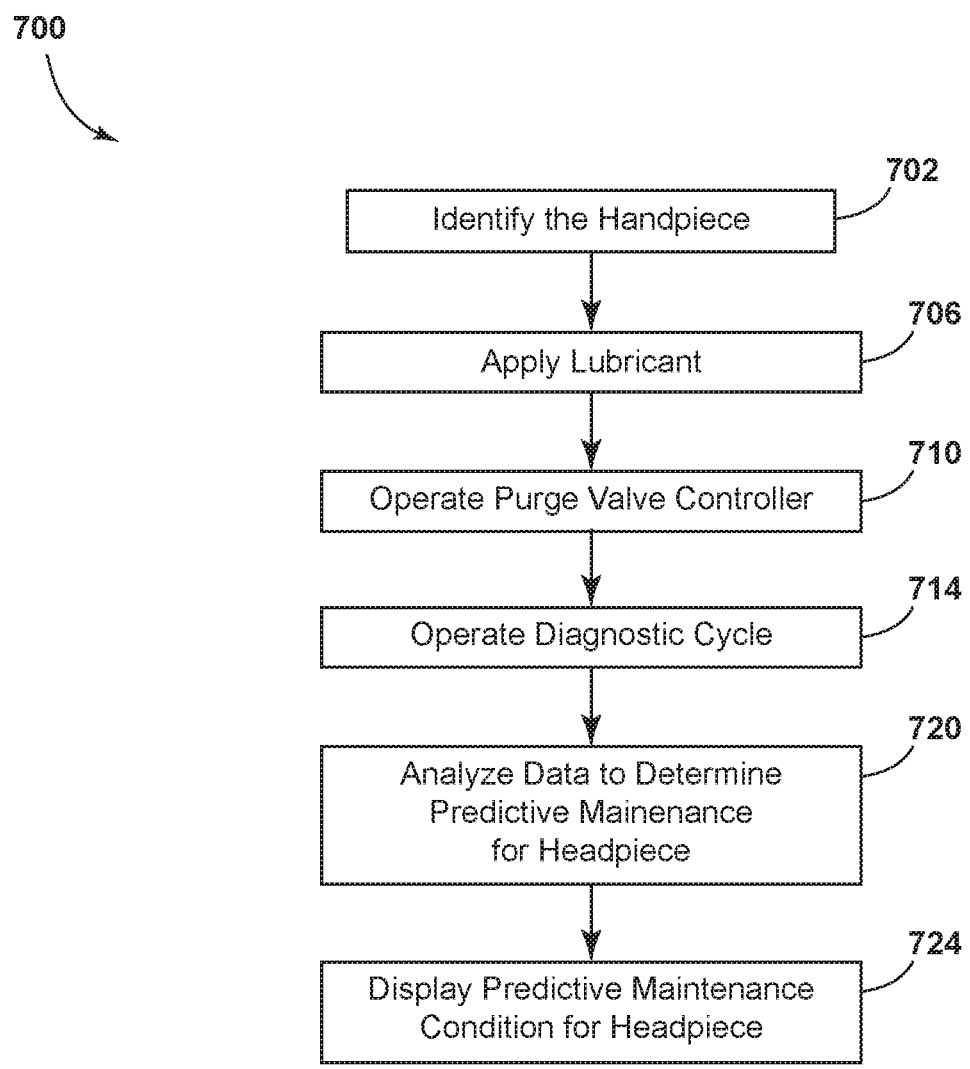
FIG. 19 illustrates a flow chart for operation of the handpiece maintenance system with an air driven handpiece.

The method for operating the handpiece maintenance system 600 is shown in the flow chart 700 of FIG. 19. In one embodiment, the nearest short range transceiver 634 of the dental handpiece maintenance system 600 reads a unique device identifier 44 from the nearby handpiece 20 (step 702) and provides the device identifier to the electronic processor 632 of the dental handpiece maintenance system 100. In the instance of a legacy handpiece 20, the operator manually enters a unique code or identifier for the handpiece with touch inputs into the GUI 629 or another device that provides the code or identifier to the electronic processor 632 (step 702) for the handpiece disposed in a specific chamber 608. The electronic processor 632 identifies the handpiece 20.

An operator actuates the spray can control 628 to control the spray of lubricant and/or cleaner to the handpiece 20 (step 706) as part of a lubrication cycle or mode via the spray valve controller 640 to the selected chamber 608.

In one embodiment, r the electronic processor 632 is configured to control the purge valve controller 650 to provide compressed air to the handpiece 20 to spread and/or remove excess lubricant from the handpiece (step 710). Thus, the handpiece 20 is lubricated by the dental handpiece maintenance system 600. The combination of steps 706, 710 define in lubrication cycle in one embodiment. While the lubrication cycle is disclosed as the maintenance cycle in FIG. 19, in another embodiment, a washing cycle and/or a sterilization cycle is contemplated.

After lubricating the handpiece 20, in the instance of a pneumatic driven handpiece 20, the electronic processor 632 operates the purge valve controller 650 to provide a diagnostic cycle or diagnostic mode wherein compressed air drives the pneumatic handpiece (step 714) and diagnostic data is obtained. The diagnostic data includes the sensing of one or more conditions of the handpiece 20 including rotational speed, temperature data and/or vibration data, and noise. Thus, changes in temperature and vibration over time are determined. In some embodiments, the diagnostic cycle (step 714) includes sensing of audio vibration data. Other sensors are contemplated.

The sensed diagnostic data is analyzed to determine predictive maintenance for the handpiece 20 (step 720). Change in temperature and/or vibration over time is analyzed by the electronic processor 632 and stored in the memory 633. In one instance an increasing change in temperature of the handpiece 20 indicates a bearing/shaft condition of the handpiece is approaching failure.

In one embodiment, the data analysis includes comparing the diagnostic data with data obtained during previous diagnostic cycles for the handpiece 20 or with data obtained during previous normal operations of the handpiece to detect unexpected results and determine a predictive maintenance condition. In another embodiment, data obtained during previous maintenance cycles for the handpiece 20 is used to determine the predictive maintenance condition of the handpiece. In another embodiment, the diagnostic data is also compared with data obtained from different handpieces 20 that are of the same model. The data from different handpieces is received from a cloud computer 220, the memory 633, or other memory storage devices.

Data analysis is executed by the electronic processor 632 of the dental handpiece maintenance system 600 in one embodiment. In another embodiment, the diagnostic data is provided to a cloud computer 220 or another computer device that performs the data analysis and sends the predictive maintenance condition to the handpiece maintenance system 600.

Figure 20:
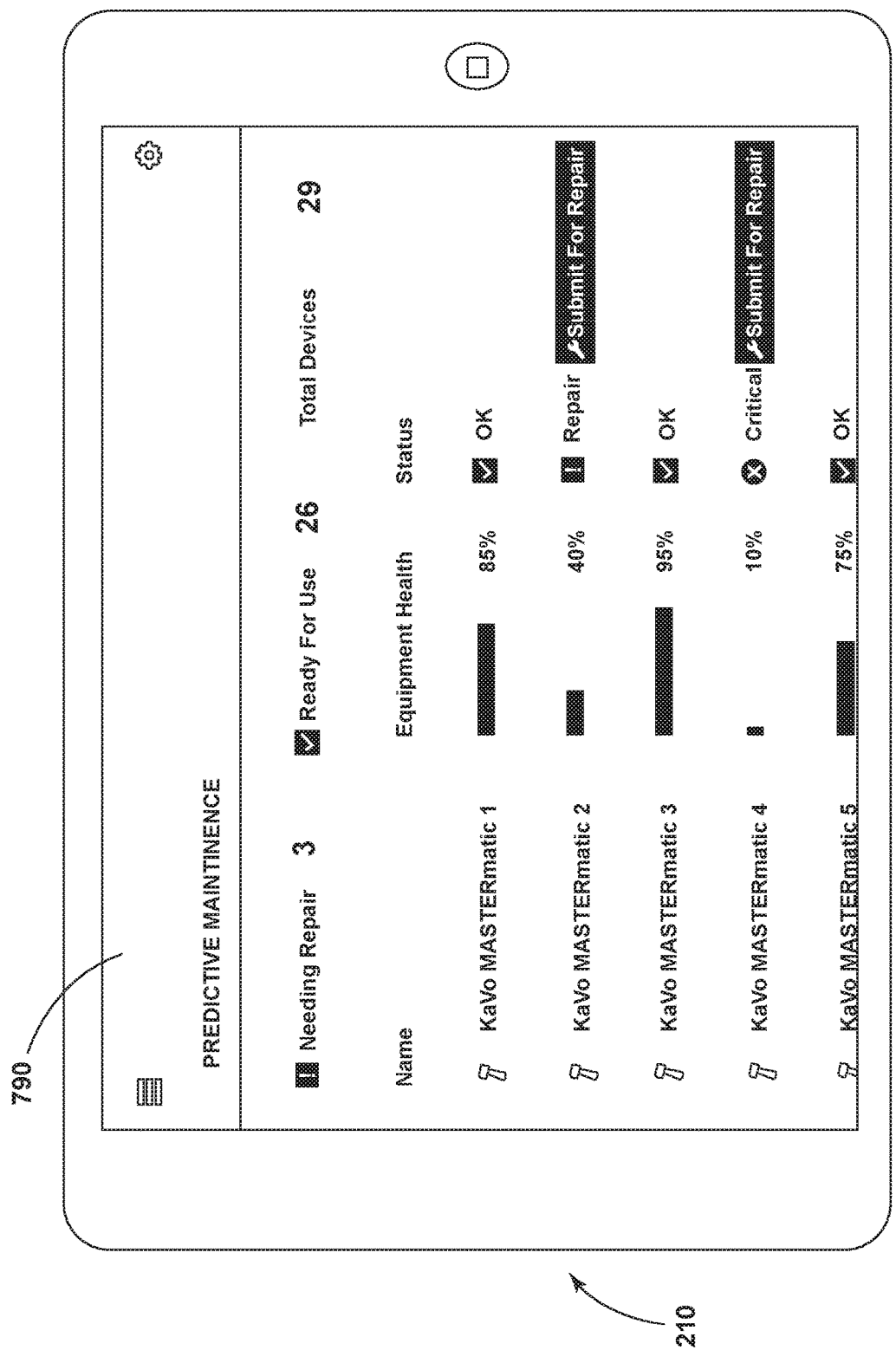
FIG. 20 illustrates a graphical user interface for a display of a universal controller.

Upon determining a predictive maintenance condition for the handpiece 20 upon completion of the diagnostic cycle, the handpiece maintenance system 600 displays the predictive maintenance condition of the handpiece (step 724) as shown in FIG. 20. The predictive maintenance condition and status of a number of handpieces are displayed as a graphical user interface 790 of the portable universal controller 210 illustrated in FIG. 20. Handpieces that are not considered usable are also indicated. The predictive maintenance condition of the handpieces disposed in the handpiece maintenance system 600 is displayed on the GUI 629 thereof after completion of the diagnostic cycle and analysis. In FIG. 20, the predictive maintenance condition is displayed as one of "OK," "Repair," and "Critical." A "Critical" condition corresponds to a shutdown condition and a "Repair" condition generally corresponds to a warning condition as shown in the flow chart of FIG. 12.

In one embodiment, the electronic processor 632 is configured for storing the predictive maintenance condition and diagnostic data, which includes the one or more sensed conditions of the handpiece 20 during the diagnostic cycle, in at least one from a group consisting of: the memory 633 of the dental handpiece maintenance system 600, a remote memory storage device, and a cloud computer 220.

While a predictive maintenance condition is determined by the electronic processor 632 of the dental handpiece maintenance system 600 in one embodiment, in another dental handpiece maintenance arrangement, a predictive maintenance determining device comprises at least one from a group consisting of: a portable universal controller 210, a computer work station 214, and a cloud computer 220. Thus, the predictive maintenance condition is determined separately using data received in part from the dental handpiece maintenance system 600.

Figure 21:
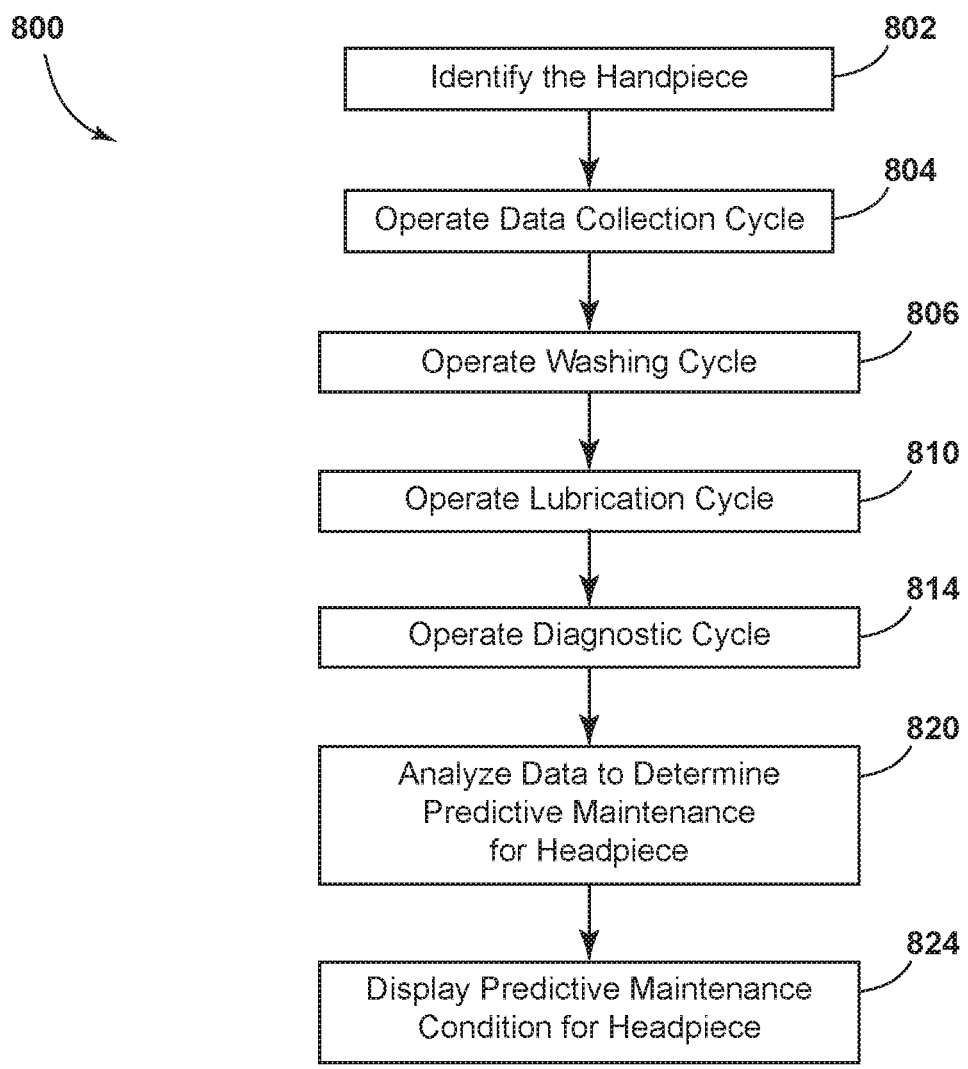
FIG. 21 illustrates a flow chart for operation of the handpiece maintenance system with an electric motor driven handpiece.

Operation of the Handpiece Maintenance System with Diagnostic Mode for Electric Motor Driven Handpiece FIG. 21 is a flow chart 800 of a method for operating the handpiece maintenance system 600, which includes operating an electric motor 670 as shown in FIGS. 15-17. The electric motor 670 operates the handpiece 20 during a diagnostic cycle for diagnostic purposes.

As in the embodiment of FIG. 19, the nearest short range transceiver 634 of the dental handpiece maintenance system 600 reads a unique device identifier 44 from the nearby handpiece 20 (step 802 in FIG. 21) and provides the device identifier to the electronic processor 632 of the dental handpiece maintenance system 100. In the instance of a legacy handpiece 20, the operator manually enters a unique code or identifier for the handpiece into the GUI 629 or other device.

For a handpiece 20 that is driven by an electric motor 670, in one embodiment the electronic processor 632 controls power to the electric motor 670 to provide a data collection cycle or diagnostic mode wherein the electric motor 670 drives the handpiece (step 804) and diagnostic data is obtained. The data collection data includes the sensing of temperature data and/or vibration data for the handpiece 20. In one embodiment, the sensors are external sensors that are built into the handpiece 20 and disposed to determine changes in temperature and vibration over time. In another embodiment, the temperature sensor 664 and acoustic sensor 660 are provided with the handpiece maintenance system 600. The data collection data includes temperature, torque, noise, along with current draw, voltage or electric motor power consumption for power that is provided to and output via the electric motor 670. The operating time and rotational speed of the electric motor are also provided as data. In some embodiments, the data collection cycle (step 804) includes sensing of audio vibration data. The data collection cycle is generally less than 30 seconds. The data collection cycle is optional.

Thereafter, in the embodiment of FIG. 21, an operator actuates the handpiece maintenance system 600 to perform a washing cycle (step 806) for the handpiece 20.

Thereafter, the handpiece maintenance system 600 operates for a lubrication cycle to lubricate the handpiece 20 (step 810). Thus, the handpiece 20 is washed and lubricated by the dental handpiece maintenance system 600.

After washing and lubricating the handpiece 20, in the instance of an electric motor driven handpiece 20, the electronic processor 632 controls the electric motor 670 to provide a diagnostic cycle or diagnostic mode, wherein the electric motor drives the handpiece (step 814) and diagnostic data is obtained. The diagnostic data includes the sensing of temperature data and/or vibration data for the handpiece 20. Thus, changes in temperature and vibration over time are determined. Further, the current draw, voltage or electric motor power consumption for power that is provided to and output via the electric motor 670 is determined over time for evaluation purposes during the diagnostic cycle (step 814). The data for evaluation purposes may include sensing the rotational speed, torque and operating time of the electric motor, along with the sensing of audio vibration data, such as noise, temperature, and/or data from other sensors during the diagnostic cycle. The diagnostic cycle is generally less than 30 seconds.

The electronic processor 632 analyzes the sensed diagnostic data, along with the collection data, to determine predictive maintenance for the handpiece 20 (step 820). Besides analyzing change in temperature and/or vibration over time, the electronic processor 632 analyzes the power data for the electric motor 670. Ambient air temperature and humidity conditions are also sensed and utilized to determine the predictive maintenance for the handpiece 20 in one embodiment. Further, the motor operating speed and operating time is analyzed. The data analysis includes comparing the diagnostic data with the collection data obtained from before the cleaning and lubricating cycle in another embodiment. In some embodiments, the data obtained during previous data collection cycles and/or diagnostic cycles for the handpiece 20, and/or data obtained during previous actual operations of the handpiece, are analyzed and combined to detect unexpected results (step 820). Data obtained during the actual and previous maintenance cycles also is used to detect the preventive maintenance condition for the handpiece 20. Further, in one embodiment the diagnostic data and the collection data is compared with data obtained from different handpieces 20 that are of the same model to determine the predictive maintenance condition of the handpiece.

As discussed above, the data analysis is executed by one or more of the electronic processor 632 of the dental handpiece maintenance system 600, the cloud computer 220, and/or another computer device that performs the data analysis. The collection data and the diagnostic data are correlated with the identified handpiece 20 and stored in the dental handpiece maintenance system 600, in the cloud computer 220, or elsewhere, for future usage.

After analysis by the electronic processor (step 820), the condition and status of the handpiece 20 is displayed on the GUI of the handpiece maintenance system 600 (step 824). In some instances, four handpieces are provided in the handpiece maintenance system 600. If so, the status of four handpieces 20 is displayed simultaneously by the GUI 629 of the handpiece maintenance system 600.

In some embodiments, the dental handpiece maintenance system 600 includes different maintenance couplings 610 that are sized to receive different handpieces 20 as shown in FIG. 14. In some embodiments, the dental handpiece maintenance system 600 includes a spray can chamber entrance, such as a door in one embodiment, for providing access to a spray container chamber that receives a spray container to provide cleaning spray therein for application to the handpieces.

The following examples illustrate example systems, methods and arrangements described herein. Example 1: a dental handpiece maintenance system for maintaining a handpiece comprising: a housing, an entrance for providing access to a chamber in the housing, at least one maintenance coupling disposed in the chamber, the maintenance coupling sized to receive a handpiece, and an electronic processor that is configured to: receive inputs from a user interface, operate a maintenance cycle for the handpiece disposed within the dental handpiece maintenance system, operate the handpiece in a diagnostic cycle while receiving one or more conditions of the handpiece, and determine a predictive maintenance condition for the handpiece from the one or more conditions received during the diagnostic cycle.

Example 2: the dental handpiece maintenance system of example 1, wherein the diagnostic cycle occurs after the maintenance cycle, and wherein the maintenance cycle includes at least one from a group of maintenance cycles consisting of: a washing cycle, a lubrication cycle, and a sterilization cycle.

Example 3: the dental handpiece maintenance system of any of examples 1 and 2, wherein the maintenance cycle comprises a lubrication cycle.

Example 4: the dental handpiece maintenance system of any of examples 1-3, wherein the maintenance cycle comprises a washing cycle and a lubrication cycle.

Example 5: the dental handpiece maintenance system of any of examples 1-4, wherein the predictive maintenance condition is displayed on the user interface of the dental handpiece maintenance system or on a portable universal controller, and wherein the predictive maintenance condition and the one or more conditions of the handpiece received during the diagnostic cycle are stored in at least one from a group consisting of: the dental handpiece maintenance system, a remote memory storage device, and a cloud computer.

Example 6: the dental handpiece maintenance system of any of examples 1-5, wherein the handpiece is an air driven handpiece, wherein operating the handpiece in the diagnostic cycle includes providing compressed air to drive the air driven handpiece, and wherein the one or more conditions include vibration, rotational speed, temperature or noise of the handpiece that is driven by the compressed air.

Example 7: the dental handpiece maintenance system of any of examples 1-6, wherein an accelerometer to sense the vibration and/or a temperature sensor to sense the temperature of the handpiece is located inside the chamber of the dental handpiece maintenance system.

Example 8: the dental handpiece maintenance system of any of examples 1-7, including a support arm disposed to support the handpiece connected to the maintenance coupling, the support arm including the accelerometer and/or the temperature sensor.

Example 9: the dental handpiece maintenance system of any of examples 1-8, wherein the maintenance coupling includes an electric motor and the handpiece is secured to and driven by the electric motor during the diagnostic cycle, and wherein the one or more conditions received during the diagnostic cycle include temperature, electric motor power consumption, rotational speed, torque or noise to determine the predictive maintenance condition.

Example 10: the dental handpiece maintenance system of any of examples 1-9, including a short range transceiver, wherein the short range transceiver is configured to sense a unique device identifier mounted to the handpiece and to provide the unique device identifier of the handpiece to the electronic processor to identify the handpiece Example 11: the dental handpiece maintenance system of any of examples 1-10, wherein the electronic processor is configured to operate the handpiece in a data collection cycle while receiving the one or more conditions of the handpiece before operating the maintenance cycle, and wherein the determining of predictive maintenance condition for the handpiece includes analyzing the one or more conditions received during the data collection cycle and during the diagnostic cycle Example 12: the dental handpiece maintenance system of any of examples 1-11, wherein the electronic processor is configured to: identify the handpiece secured to the maintenance coupling, determine the predictive maintenance condition for the handpiece from the one or more conditions received during the diagnostic cycle and from the one or more conditions received during previous diagnostic cycles of the handpiece that are stored in a memory of the dental handpiece maintenance system or a cloud computer in communication with the dental handpiece maintenance system, and display the predictive maintenance condition, wherein the user interface displays a status of the dental handpiece maintenance system.

Example 13: a method of operating a dental handpiece maintenance system having a housing and at least one maintenance coupling for receiving a dental handpiece comprising: providing a handpiece secured on the maintenance coupling disposed in a chamber of the dental handpiece maintenance system; operating the dental handpiece maintenance system in a maintenance cycle; subsequently operating the handpiece in a diagnostic cycle while sensing one or more conditions of the handpiece; and determining a predictive maintenance condition for the handpiece from the one or more conditions sensed during the diagnostic cycle.

Example 14: the method of example 13, including identifying the handpiece by receiving inputs identifying the handpiece on a user interface of the dental handpiece maintenance system, and wherein the diagnostic cycle occurs after the maintenance cycle.

Example 15: the method of any of examples 13 and 14, wherein the determining of the predictive maintenance condition is determined by one from a group consisting of: an electronic processor of the dental handpiece maintenance system, a portable universal controller, a computer work station, and a cloud computer.

Example 16: the method of any of examples 13-15, including a further step of storing the predictive maintenance condition and the one or more conditions of the handpiece sensed during the diagnostic cycle in at least one from a group consisting of: the dental handpiece maintenance system, a remote memory storage device, and a cloud computer, and displaying the predictive maintenance condition on a user interface of the dental handpiece maintenance system or on a portable universal controller.

Example 17: the method of any of examples 13-16, wherein the handpiece is an air driven handpiece, and the operating of the handpiece in the diagnostic cycle includes providing compressed air to drive the air driven handpiece, and wherein the sensed conditions include vibration, rotational speed, temperature or noise of the handpiece that is driven by the compressed air.

Example 18: the method of any of examples 13-17, further comprising operating the handpiece in a data collection cycle while sensing the one or more conditions of the handpiece before the operating of the maintenance cycle, and wherein the determining of the predictive maintenance condition for the handpiece includes analyzing the one or more conditions from the data collection cycle and from the diagnostic cycle Example 19: the method of any of examples 13-18, wherein the determining of the predictive maintenance condition for the handpiece includes analyzing the one or more conditions from during the diagnostic cycle and analyzing the one or more conditions from previous diagnostic cycles or usage data collected during normal operation of the handpiece that are stored in a memory of the dental handpiece maintenance system or a cloud computer in communication with the dental handpiece maintenance system Example 20: the method of any of examples 13-19, wherein operating the dental handpiece maintenance system in the maintenance cycle includes at least one from a group consisting of: operating for a washing cycle, operating for a lubrication cycle, and operating for a sterilization cycle.

Example 21: the method of any of examples 13-20, wherein operating the dental handpiece maintenance system in the maintenance cycle includes operating for each of a washing cycle, a lubrication cycle, and a sterilization cycle.

Example 22: a dental handpiece maintenance arrangement for maintaining a handpiece comprising: a dental handpiece maintenance system including a housing, an entrance for providing access to a chamber in the housing, at least one maintenance coupling disposed in the chamber, the maintenance coupling sized to receive a handpiece, and an electronic processor that is configured to: receive inputs from a user interface, operate a maintenance cycle for the handpiece disposed within the dental handpiece maintenance system, and operate the handpiece in a diagnostic cycle while receiving one or more conditions of the handpiece, and a predictive maintenance determining device for determining a predictive maintenance condition for the handpiece from the one or more conditions received during the diagnostic cycle.

Example 23: the dental handpiece maintenance arrangement of example 22, wherein the maintenance cycle occurs before the diagnostic cycle, and wherein the predictive maintenance determining device comprises at least one from a group consisting of: a portable universal controller, a computer work station, and a cloud computer Example 24: a method of providing predictive maintenance for a dental handpiece or component thereof, comprising: wirelessly receiving sensor data from a handpiece memory; receiving usage data for the dental handpiece; determining a predictive maintenance condition of the dental handpiece based on at least one of the sensor data and the usage data of the dental handpiece, and displaying a preventative maintenance indication for the dental handpiece.

Example 25: the method of example 24, wherein an increased severity of the predictive maintenance condition results in one or more from a group consisting of: a preventive maintenance warning of an approaching failure of the dental handpiece and a disabling of operation of the dental handpiece.

Example 26: the method of any of examples 24 and 25, wherein the determining of the predictive maintenance condition of the dental handpiece includes analyzing temperature data and change of temperature data, and providing a preventive maintenance warning to an operator or disabling operation of the dental handpiece based on the analysis.

Example 27: the method of any of examples 24-26, wherein the sensor data includes at least one of physical vibration data and temperature data for the dental handpiece, and the determining of the predictive maintenance condition of the dental handpiece includes determining a bearing/shaft condition of the dental handpiece, and providing a preventive maintenance warning when the bearing/shaft condition indicates an approaching failure for the dental handpiece.

Example 28: the method of any of examples 24-27, wherein the sensor data and the usage data includes vibration data, temperature data from temperature sensors disposed near the bearings of the dental handpiece, handpiece operating speeds, handpiece operating times, ambient air temperature, and humidity conditions, and the determining of the predictive maintenance condition of the dental handpiece providing the preventive maintenance indication for multiple conditions.

Example 29: a handpiece of a delivery unit for use with a treatment unit, the handpiece comprising: a housing; a sensor for sensing a condition of the handpiece; a handpiece memory for storing data; and an electronic processor configured to repeatedly receive the condition from the sensor and repeatedly store the condition as sensor data in the handpiece.

Example 30: the handpiece of example 29, wherein the sensor is a vibration sensor for sensing vibration data for the handpiece, the handpiece further comprising: a unique device identifier for specific identification of the handpiece; and a temperature sensor for sensing temperature data for the handpiece.

Example 31: the handpiece of any of examples 29 and 30, wherein the temperature sensor is disposed near an end cap at a distal end of the handpiece to sense the temperature data.

Example 32: the handpiece of any of examples 29-31, wherein the electronic processor is configured to receive the vibration data and the temperature data, and time stamp and store the vibration data and the temperature data as the sensor data in the handpiece memory.

Example 33: the handpiece of any of examples 29-32, wherein the sensor is a vibration sensor, the handpiece further comprising a microphone for sensing sound to generate sound data; and a force sensor for sensing force applied by the handpiece to generate force data, wherein the electronic processor is configured to receive the force data, the vibration data, and the sound data, and time stamp and store the force data, the vibration data, and the sound data as the sensor data in the handpiece memory.

Thus, the embodiments provide, among other things, a dental handpiece maintenance system that includes a diagnostic cycle for operating a handpiece to determine a predictive maintenance condition thereof and an arrangement wherein a handpiece repeatedly stores sensor data to obtain a historical usage data for handpiece operation. Various features and advantages of the embodiments are set forth in the following claims.

What is claimed is:

1. A dental handpiece maintenance system for maintaining a handpiece comprising:
a housing;
an entrance for providing access to a chamber in the housing;
at least one maintenance coupling disposed in the chamber, the maintenance coupling sized to receive a handpiece;
an accelerometer to sense vibration and/or a temperature sensor to sense temperature of the handpiece located inside the chamber;
a support arm disposed to support the handpiece connected to the maintenance coupling, the support arm including the accelerometer and/or the temperature sensor; and
an electronic processor that is configured to:
receive inputs from a user interface,
operate a maintenance cycle for the handpiece disposed within the dental handpiece maintenance system,
operate the handpiece in a diagnostic cycle while receiving one or more conditions of the handpiece, and
determine a predictive maintenance condition for the handpiece from the one or more conditions received during the diagnostic cycle.

2. The dental handpiece maintenance system according to claim 1, wherein the diagnostic cycle occurs after the maintenance cycle, and wherein the maintenance cycle includes at least one from a group of maintenance cycles consisting of: a washing cycle, a lubrication cycle, and a sterilization cycle.

3. The dental handpiece maintenance system according to claim 1, wherein the maintenance cycle comprises a lubrication cycle.

4. The dental handpiece maintenance system according to claim 1, wherein the maintenance cycle comprises a washing cycle and a lubrication cycle.

5. The dental handpiece maintenance system according to claim 1, wherein the predictive maintenance condition is displayed on the user interface of the dental handpiece maintenance system or on a portable universal controller, and
wherein the predictive maintenance condition and the one or more conditions of the handpiece received during the diagnostic cycle are stored in at least one from a group consisting of: the dental handpiece maintenance system, a remote memory storage device, and a cloud computer.

6. The dental handpiece maintenance system according to claim 1, wherein the handpiece is an air driven handpiece, wherein operating the handpiece in the diagnostic cycle includes providing compressed air to drive the air driven handpiece, and wherein the one or more conditions include vibration, rotational speed, temperature or noise of the handpiece that is driven by the compressed air.

* * * * *